United States Patent [19]
Nataraj et al.

[11] Patent Number: 6,110,979
[45] Date of Patent: *Aug. 29, 2000

[54] UTILIZATION OF SYNTHESIS GAS PRODUCED BY MIXED CONDUCTING MEMBRANES

[75] Inventors: Shankar Nataraj; Steven Lee Russek, both of Allentown, Pa.

[73] Assignee: Air Products and Chemicals, Inc., Allentown, Pa.

[*] Notice: This patent is subject to a terminal disclaimer.

[21] Appl. No.: 09/157,544

[22] Filed: Sep. 21, 1998

Related U.S. Application Data

[63] Continuation-in-part of application No. 08/997,642, Dec. 23, 1997, Pat. No. 6,048,472.

[51] Int. Cl.$^7$ .......................................................... C01B 3/26
[52] U.S. Cl. ........................... 518/704; 252/373; 423/652
[58] Field of Search .................................... 423/650, 652, 423/655, 656; 252/373; 518/704

[56] References Cited

U.S. PATENT DOCUMENTS

| | | | |
|---|---|---|---|
| 4,079,017 | 3/1978 | Crawford et al. | 252/373 |
| 4,791,079 | 12/1988 | Hazbun | 502/4 |
| 4,793,904 | 12/1988 | Mazanec et al. | 204/59 R |
| 4,822,521 | 4/1989 | Fuderer | 252/373 |
| 5,160,713 | 11/1992 | Mazanec et al. | 423/648.1 |
| 5,276,237 | 1/1994 | Mieville | 585/500 |
| 5,306,411 | 4/1994 | Mazanec et al. | 204/265 |
| 5,356,728 | 10/1994 | Balachandran et al. | 429/8 |
| 5,536,488 | 7/1996 | Mansour et al. | 423/652 |
| 5,580,497 | 12/1996 | Balachandran et al. | 252/519 |
| 5,591,315 | 1/1997 | Mezanec et al. | 205/462 |
| 5,599,383 | 2/1997 | Dyer et al. | 96/8 |

FOREIGN PATENT DOCUMENTS

| | | | |
|---|---|---|---|
| 0399833 | 11/1990 | European Pat. Off. | B01D 71/02 |
| 0732138 | 9/1996 | European Pat. Off. | B01D 53/22 |

OTHER PUBLICATIONS

Rostrup–Nielsen, J. et al., "Steam Reforming–Opportunities and Limits of the Technology", presented at the NATO ASI Study on Chemical Reactor Technology for Environmentally Safe Reactors and Predictors, Aug. 25–Sep. 5, 1991, Ontario, Canada.

Christiansen, T. S. et al. "Improve Syngas Production Using Autothermal Reforming", *Hydrocarbon Processing*, Mar. 1994, pp. 39–46.

Sundset, T. et al., "Evaluation of Natural Gas Based Synthesis Gas production Technologies", *Catalysis Today* 21 (1994), pp. 269–278, (No Month).

Reed, C.L. et al., "Production of Synthesis Gas by Partial Oxidation of Hydrocarbons" presented at the 86$^{th}$ AIChE meeting, Houston, Texas, Apr. 1–5, 1979.

Fong, F., "Texaco's HyTEX Process for High Pressure Hydrogen Production", presented at the KTI Symposium, Apr. 27, 1993, Caracas, Venezuela.

(List continued on next page.)

*Primary Examiner*—Wayne Langel
*Attorney, Agent, or Firm*—John M. Fernbacher

[57] ABSTRACT

Hydrocarbon feedstocks are converted into synthesis gas in a two-stage process comprising an initial steam reforming step followed by final conversion to synthesis gas in a mixed conducting membrane reactor. The steam reforming step converts a portion of the methane into synthesis gas and converts essentially all of the hydrocarbons heavier than methane into methane, hydrogen, and carbon oxides. The steam reforming step produces an intermediate feed stream containing methane, hydrogen, carbon oxides, and steam which can be processed without operating problems in a mixed conducting membrane reactor. The steam reforming and mixed conducting membrane reactors can be heat-integrated for maximum operating efficiency and produce synthesis gas with compositions suitable for a variety of final products. Synthesis gas produced by the methods of the invention is further reacted to yield liquid hydrocarbon or oxygenated organic liquid products.

29 Claims, 6 Drawing Sheets

OTHER PUBLICATIONS

Osterrieth, P. J. et al., "Custom–Made Synthesis Gas Using Texaco's Partial Oxidation Technology", presented at the AIChE Spring National Meeting, New Orleans, LA, Mar. 9, 1988.

Balachandran, U. et al. "Ceramic Membranes For Methane Conversion", presented at the Coal Liquefaction and Gas Conversion Contractors, Review Conference, Sep. 7–8, 1994, Pittsburgh, PA.

Tsai, C.–Y. et al., "Simulation of a Nonisothermal Catalytic Membrane Reactor for Methane partial Oxidation to Syngas", Proceedings of the Third International Conference of Inorganic Membranes, Worcester, MA, Jul. 10–14, 1994.

Tsai, C.–Y. et al., "Modeling and Simulation of a Nonisothermal Catalytic Membrane Reactor", *Chem. Eng Comm.*, 1995, vol. 134, pp. 107–132.

Tsai, C. Y., "Perovskite Dense Membrane Reactors for the Partial Oxidation of Methane to Synthesis Gas", May 1996 (published by UMI Dissertation Services).

Cromarty, B. J. et al., "The Application of Pre–Reforming Technology in the Production of Hydrogen", presented at the NPRA Annual Meeting, Mar. 21–23, 1993, San Antonio, Texas.

Foreman, J. M., et al., "The Benefits of pre–reforming in Hydrogen Production Plants", presented at th World Hydrogen Conference, Jun. 1992.

Cromarty, B. J., "Modern Aspects of Steam Reforming for Hydrogen Plants", presented at the World Hydrogen Confernece, Jun. 1992.

Mazanec, T. J., "Electropox Gas Reforming", Electrochemical Society Proceedings, vol. 95–24, 16 1997, pp. 16–28, (No Month).

U.S. application No. 08/721,640, Adler et al., filed Sep. 26, 1996.

U.S. application No. 08/997,642, Nataraj et al., filed Dec. 23, 1997.

U.S. application No. 08/870,012, Nataraj et al., filed Jun. 6, 1997.

U.S. application No. 09/141,909, Adler et al., filed Aug. 28, 1998.

U.S. application No. 09/157,712, Nataraj et al., filed Sep. 21, 1998.

Copy of European Search Report.

UTILIZATION OF SYNTHESIS GAS PRODUCED BY MIXED CONDUCTING MEMBRANES

CROSS-REFERENCE TO RELATED APPLICATIONS

This application is a Continuation-in-Part of Ser. No. 08/997,642, filed on Dec. 23, 1997, U.S. Pat. No. 6,048,472, which is incorporated herein by reference.

STATEMENT REGARDING FEDERALLY SPONSORED RESEARCH OR DEVELOPMENT

Not applicable.

BACKGROUND OF THE INVENTION

Synthesis gas containing hydrogen and carbon oxides is an important feedstock for the production of a wide range of chemical products. Synthesis gas mixtures with the proper ratios of hydrogen to carbon monoxide are reacted catalytically to produce liquid hydrocarbons and oxygenated organic compounds including methanol, acetic acid, dimethyl ether, oxo alcohols, and isocyanates. High purity hydrogen and carbon monoxide are recovered by further processing and separation of synthesis gas. The cost of generating the synthesis gas usually is the largest part of the total cost of these products.

Two major reaction routes are used for synthesis gas production—steam reforming of light hydrocarbons, primarily natural gas, naphtha, and refinery offgases, and the partial oxidation of carbon-containing feedstocks ranging from natural gas to high molecular weight liquid or solid carbonaceous materials. Autothermal reforming is an alternative process using light hydrocarbon feed in which both partial oxidation and steam reforming reactions occur in a single reactor. In the various versions of autothermal reforming, feed gas is partially oxidized in a specially-designed burner and the resulting hot gas passes through a catalyst bed where steam reforming and $CO_2$ reforming occur. Newer synthesis gas generation processes include various heat exchange reformers such as gas heated reforming (GHR) developed by ICI, the SMART reformer by KTI, and the CAR reformer by UHDE; the improved Texaco gasification process (TGP) included in their HyTEX™ hydrogen production system; Haldor-Topsoe's HERMES process; the Shell gasification process (SGP); Exxon's fluidized bed synthesis gas process; and Kellogg's KRES process.

The state of the art in commercial synthesis gas generation technology is summarized in representative survey articles including "Steam Reforming—Opportunities and Limits of the Technology" by J. Rostrup-Nielsen et al, presented at the NATO ASI Study on Chemical Reactor Technology for Environmentally Safe Reactors and Predictors, Aug. 25–Sep. 5, 1991, Ontario, Canada; "Improve Syngas Production Using Autothermal Reforming" by T. S. Christiansen et al, *Hydrocarbon Processing*, March 1994, pp. 39–46; "Evaluation of Natural Gas Based Synthesis Gas Production Technologies" by T. Sundset et al, *Catalysis Today*, 21 (1994), pp. 269–278; "Production of Synthesis Gas by Partial Oxidation of Hydrocarbons" by C. L. Reed et al, presented at the 86th National AlChE meeting, Houston, Tex., Apr. 1–5, 1979; "Texaco's HyTEX™ Process for High Pressure Hydrogen Production" by F. Fong, presented at the KTI Symposium, Apr. 27, 1993, Caracas, Venezuela; and "Custom-Made Synthesis Gas Using Texaco's Partial Oxidation Technology" by P. J. Osterrieth et al, presented at the AlChE Spring National Meeting, New Orleans, La., Mar. 9, 1988.

Staged steam-methane reforming processes are used to upgrade the performance of existing plants and for the design of more efficient new plants for producing synthesis gas. One type of staged reforming utilizes a prereformer, typically an adiabatic reforming reactor containing a highly active nickel catalyst, to reform heavier hydrocarbons in the feedstock (and a portion of the methane, if present) to yield a mixture of methane, hydrogen, carbon monoxide, carbon dioxide, and steam. This prereforming product is then further processed in a fired tubular reformer to produce a raw synthesis gas product. Another type of staged reformer process utilizes a gas heated reformer (GHR) followed by an autothermal reformer. The GHR is a type of heat exchange reformer in which the hot raw synthesis gas from the autothermal reformer furnishes the heat for the first reforming stage in the GHR.

Staged reforming processes are described in papers entitled "The Application of Pre-Reforming Technology in the Production of Hydrogen" by B. J. Cromarty et al, presented at the NPRA Annual Meeting, Mar. 21–23, 1993, San Antonio, Tex.; "The Benefits of Pre-reforming in Hydrogen Production Plants" by J. M. Foreman et al, presented at the World Hydrogen Conference, June 1992; and "Modern Aspects of Steam Reforming for Hydrogen Plants" by B. J. Cromarty, presented at the World Hydrogen Conference, June 1992. Gas heated reforming is described in a paper by K. J. Elkins et al entitled "The ICI Gas-Heated Reformer (GHR) System" presented at the Nitrogen '91 International Conference, Copenhagen, June 1992.

Other combinations of steam reforming and autothermal reforming are used in synthesis gas production. In the production of ammonia synthesis gas, for example, a combination of steps called primary reforming and secondary reforming is used in which natural gas is steam reformed and the resulting intermediate product is further converted in an air-fired autothermal reforming reactor to yield raw ammonia synthesis gas containing hydrogen, nitrogen, and carbon monoxide. Primary steam reforming followed by oxygen secondary reforming (autothermal reforming) is used in the production of synthesis gas containing hydrogen and carbon monoxide in which secondary reforming is carried out in an oxygen-fired autothermal reformer. Primary steam reforming can be carried out in a fired tubular reformer.

In the commercial processes described above which utilizes an autothermal reforming step, oxygen is required and is typically supplied at purities of 95 to 99.9 vol %. Oxygen is obtained by the separation of air using known methods, usually the low-temperature distillation of air for larger volumes and pressure swing adsorption for smaller volumes.

The conversion of synthesis gas into a wide variety of products is well known in the art as described in compendia such as the *Kirk-Othmer Encyclopedia of Chemical Technology*, 4th Edition, 1991, Wiley-Interscience, New York. Two of the largest volume consumers of synthesis gas in the chemical process industries are the Fischer-Tropsch process for the synthesis of higher molecular weight hydrocarbons and the various gas-phase and liquid-phase methanol synthesis processes. These high-volume products find use as fuels and as chemical intermediates for further product synthesis.

Synthesis gas can be reacted in three-phase slurry reactors to yield methanol and dimethyl ether, useful as alternative fuels or chemical intermediates, as described in U.S. Pat. Nos. 4,910,227; 5,179,129; 5,218,003; and 5,284,878.

An alternative technology for synthesis gas production is in the early stages of development in which oxygen for the partial oxidation reactions is provided in situ by the separation of air at high temperatures using ceramic, ceramic-metal, or ceramic-ceramic composite membranes which conduct both electronic species and oxygen ions. These membranes are included in a broad class of membranes known generically as ion transport membranes, and form a specific class of ion transport membranes known collectively as mixed conducting membranes which conduct both electronic species and oxygen ions. These membranes can be used optionally in combination with appropriate catalysts to produce synthesis gas in a membrane reactor without the need for a separate oxygen production unit. The reactor is characterized by one or more reaction zones wherein each zone comprises a mixed conducting membrane which separates the zone into an oxidant side and a reactant side.

An oxygen-containing gas mixture, typically air, is contacted with the oxidant side of the membrane and oxygen gas reacts with electronic species to form oxygen ions which permeate through the membrane material. A reactant gas containing methane and other low molecular weight hydrocarbons flows across the reactant side of the membrane. Oxygen (as defined later) on the reactant side of the membrane reacts with components in the reactant gas to form synthesis gas containing hydrogen and carbon monoxide. A catalyst to promote the transfer of oxygen into the membrane can be applied to the surface of the membrane on the oxidant side. A catalyst to promote the conversion of reactant gas components to synthesis gas may be applied to the surface of the reactant side of the membrane; alternatively or additionally, a granular form of the catalyst may be placed adjacent to the membrane surface. Catalysts which promote the conversion of hydrocarbons, steam, and carbon dioxide to synthesis gas are well-known in the art.

Numerous reactors and compositions of mixed conducting membranes suitable for this purpose have been disclosed in the art. Membrane reactors and methods of operating such reactors for the selective oxidation of hydrocarbons are disclosed in related U.S. Pat. Nos. 5,306,411 and 5,591,315. Ceramic membranes with wide ranges of compositions are described which promote the transfer of oxygen from an oxygen-containing gas and reaction of the transferred oxygen with a methane-containing gas to form synthesis gas. Mixed conductors having a perovskite structure are utilized for the membrane material; alternatively multiphase solids are used as dual conductors wherein one phase conducts oxygen ions and another conducts electronic species. A membrane reactor to produce synthesis gas is disclosed which operates at a temperature in the range of 1000 to 1400° C., wherein the reactor may be heated to the desired temperature and the temperature maintained during reaction by external heating and/or exothermic heat from the chemical reactions which occur. In one general embodiment, it is disclosed that the process is conducted at temperatures within the range of 1000 to 1300° C. Experimental results are reported for oxygen flux and synthesis gas production in an isothermal laboratory reactor using a dual-conducting membrane at a constant temperature of 1100° C. Inert diluents such as nitrogen, argon, helium, and other gases may be present in the reactor feed and do not interfere with the desired chemical reactions. Steam if present in the reactor feed is stated to be an inert gas or diluent.

In a paper entitled "Ceramic Membranes for Methane Conversion" presented at the Coal Liquefaction and Gas Conversion Contractors, Review Conference, Sep. 7–8, 1994, Pittsburgh, Pa., U. Balachandran et al describe the fabrication of long tubes of $Sr—Co_{0.5}—Fe—O_x$ membranes and the operation of these tubes for conversion of methane to synthesis gas in laboratory reactors at 850° C.

U.S. Pat. No. 4,793,904 discloses the use of a solid electrolyte membrane with conductive coatings on both sides which are optionally connected by an external circuit. The membrane is used in an electrolytic cell at temperatures in the range of 1050 to 1300° C. to convert methane to synthesis gas at a pressure of about 0.1 to about 100 atmospheres. Experimental results are presented for the conversion of methane to synthesis gas components in a reactor cell with an yttria-stabilized zirconia membrane having platinum electrodes optionally using an external electrical circuit. The reactor cell was operated isothermally at a temperature of 800, 1000, or 1100° C.

Related U.S. Pat. Nos. 5,356,728 and 5,580,497 disclose cross-flow electrochemical reactor cells and the operation of these cells to produce synthesis gas from methane and other light hydrocarbons. Mixed conducting membranes made of mixed oxide materials are disclosed for use in the crossflow reactor cells. The production of synthesis gas by the partial oxidation of hydrocarbons is disclosed using reactor temperatures of about 1000 to 1400° C. or alternatively in the range of about 450 to 1250° C. Experimental results are reported for synthesis gas production in isothermal tubular laboratory reactors at constant temperatures in the range of 450 to 850° C. A pressure in the ceramic tube reactor, typically about 6 inches of water head, was maintained by means of a downstream water bubbler.

U.S. Pat. No. 5,276,237 discloses the partial oxidation of methane to synthesis gas using a mixed metal oxide membrane comprising alumina with multivalent activator metals such as yttrium and barium. A process concept is disclosed with low oxygen recovery to facilitate heat removal and maintain a high oxygen partial pressure driving force. The partial oxidation reactions were carried out at a temperature in the range of about 500 to about 1200° C., and the temperature on the oxygen side of the membrane is described to be at most only a few degrees less than the reaction temperature on the reactant side of the membrane.

The practical application of mixed conducting membranes to produce synthesis gas will require reactor modules having a plurality of individual membranes with appropriate inlet and outlet flow manifolds to transport feed and product gas streams. Such modules provide the large membrane surface area required to produce commercial volumes of synthesis gas product. A number of membrane module designs have been disclosed in the art which address this requirement. Previously-cited U.S. Pat. Nos. 5,356,728 and 5,580,497 describe one type of crossflow membrane reactor which has hollow ceramic blades positioned across a gas stream flow or a stack of crossed hollow ceramic blades containing channels for gas flow. Alternatively, the crossflow reactor can be fabricated in the form of a monolithic core with appropriate inlet and outlet manifolding. U.S. Pat. No. 4,791,079 discloses membrane module designs for mixed conducting membrane reactors for the oxidative coupling of methane to produce higher hydrocarbons, hydrogen, and carbon oxides.

A planar membrane module is described in U.S. Pat. No. 5,681,373 which contains a plurality of planar units each of which comprises a channel-free porous support with an outer layer of mixed conducting oxide material. An oxygen-containing gas is passed through the porous supports and permeated oxygen reacts with light hydrocarbons at the outer layer of the mixed conducting oxide material. The module is heated to a temperature ranging from about 300 to 1200° C. for continuous production of synthesis gas. U.S. Pat. No. 5,599,383 discloses a tubular solid state membrane module having a plurality of mixed conducting tubes each of which contains inner porous material which supports the tube walls and allows gas flow within the tube. The module can be used to produce synthesis gas wherein an oxygen-containing gas is passed through the inside of the tubes and a hydrocarbon-containing gas is passed over the outside of the tubes. The module is heated to a temperature ranging from 300 to 1200° C., the oxygen-containing gas is passed through the tubes, and the hydrocarbon-containing gas is passed over the outside of the tubes. Oxygen permeates through the mixed conducting tube walls and reacts with the hydrocarbon under controlled conditions to produce synthesis gas containing hydrogen and carbon monoxide. A catalyst to promote the formation of synthesis gas may be applied to the outer surface of the tubes.

The background art summarized above characterizes the temperatures and pressures in mixed conducting membrane reactors for synthesis gas production in general non-spatial terms, that is, differences in temperature and pressure as a function of reactor geometry are not considered. All of the above disclosures teach the operation of reactors at a single temperature, i.e., as isothermal reactors, particularly for laboratory-scale reactors. In some cases, general temperature ranges are disclosed for reactor operation, but no information is offered regarding how the temperature varies with reactor geometry. In all cases, gas pressures are reported as single pressures independent of geometry, and no pressure differences between the oxidant (air) side and the hydrocarbon (fuel) side are disclosed.

C.-Y. Tsai et al describe a nonisothermal, two-dimensional computational model of a mixed conducting membrane reactor using a perovskite membrane for the partial oxidation of methane to synthesis gas. This work is presented in related publications entitled "Simulation of a Nonisothermal Catalytic Membrane Reactor for Methane Partial Oxidation to Syngas" in the Proceedings of the Third International Conference on Inorganic Membranes, Worcester Mass., Jul. 10–14, 1994, and "Modeling and Simulation of a Nonisothermal Catalytic Membrane Reactor" in *Chem. Eng Comm.*, 1995, Vol. 134, pp. 107–132. The simulation describes the effects of gas flow rate, reactor length, and membrane thickness on methane conversion and synthesis gas selectivity for a tubular reactor configuration with air on the shell side. Temperature profiles as a function of axial reactor position are also presented. Key parameters are held constant for all simulation cases; in particular, the pressure for both shell and tube sides of the reactor is specified at 1 atm and the inlet temperature is specified at 800° C. Additional discussion of experimental and computational work on topics in these two publications is presented in the doctoral thesis by C.-Y. Tsai entitled "Perovskite Dense Membrane Reactors for the Partial Oxidation of Methane to Synthesis Gas", May 1996, Worcester Polytechnic Institute (available through UMI Dissertation Services).

The practical application of mixed conducting membranes to produce synthesis gas requires reactor modules with a plurality of individual membranes having appropriate inlet and outlet flow manifolds to transport feed and product gas streams. The successful operation of such reactor modules will require the careful selection and control of inlet, intermediate, and outlet gas temperatures, since these temperatures will affect both the chemical reactions which occur in the reactor and the mechanical integrity of the reactor assembly. In addition, the gas pressures within the reactor will affect product distribution, reactor integrity, gas compression equipment, and power requirements; therefore, the gas pressures must be specified carefully in the design and operation of reactor modules. The prior art to date has not addressed these important design and operating issues.

Synthesis gas production using mixed conducting membrane reactors also will involve the integration of reactor modules with feed gas supply systems and with product gas treatment and separation systems. Further, the proper combination of reaction conditions and reactant gas feed composition must be utilized to ensure proper reactor operation. This integration of mixed conducting membrane reactors into overall process designs for synthesis gas production has not been addressed in the prior art.

The successful design and operation of synthesis gas production systems which utilize mixed conducting membrane reactors will depend upon the proper integration of the reactors with upstream and downstream gas processing systems. Such downstream gas processing systems include the conversion of the synthesis gas into liquid products such as liquid hydrocarbons and oxygenated organic compounds including methanol, acetic acid, dimethyl ether, oxo alcohols, and isocyanates. The invention described below and defined in the claims which follow addresses these practical design and operating requirements for synthesis gas production in membrane reaction systems and the use of synthesis gas in downstream conversion processes.

BRIEF SUMMARY OF THE INVENTION

The invention is a method for the production and utilization of synthesis gas containing hydrogen and carbon monoxide which comprises:

(a) providing a catalytic reforming reaction zone comprising at least one catalyst which promotes the steam reforming of hydrocarbons;

(b) heating a reactant gas feed comprising steam and one or more hydrocarbons, introducing the resulting heated reactant gas feed into the catalytic reforming reaction zone, and withdrawing therefrom a partially reformed intermediate gas comprising at least methane, hydrogen, and carbon oxides;

(c) providing a mixed conducting membrane reaction zone having an oxidant side and a reactant side which are separated by a solid mixed conducting membrane;

(d) heating an oxygen-containing oxidant gas feed and introducing the resulting heated oxidant gas feed into the oxidant side of the mixed conducting membrane reactor;

(e) introducing the partially reformed intermediate gas into the reactant side of the mixed conducting membrane reactor;

(f) permeating oxygen from the oxidant side of the mixed conducting membrane reactor through the mixed conducting membrane to the reactant side of the mixed conducting membrane reactor and reacting the oxygen with the partially reformed intermediate gas to form additional hydrogen and carbon monoxide;

(g) withdrawing a raw synthesis gas product comprising hydrogen, carbon monoxide, carbon dioxide, and water from the reactant side of the mixed conducting membrane reactor;

(h) withdrawing an oxygen-depleted nonpermeate gas from the oxidant side of the mixed conducting membrane reactor;

(i) treating the raw synthesis gas to remove at least a portion of a component other than hydrogen and carbon monoxide to yield a final synthesis gas product, and (j) providing a product synthesis and processing zone and converting at least a portion of the final synthesis gas product therein to yield a liquid product.

The invention optionally may further comprise the step of heating the partially reformed intermediate gas. The reactant gas feed can comprise methane, or alternatively can comprise one or more hydrocarbon compounds having two or more carbon atoms.

At least a portion of the heat for heating the oxygen-containing oxidant gas feed can be provided by indirect heat exchange with at least a portion of the oxygen-depleted nonpermeate gas from the oxidant side of the mixed conducting membrane reactor. At least a portion of the heat for heating the reactant gas feed can be provided by indirect heat exchange with at least a portion of the oxygen-depleted nonpermeate gas from the oxidant side of the mixed conducting membrane reactor. Alternatively, at least a portion of the heat for heating the oxygen-containing oxidant gas feed can be provided by direct combustion of a portion of the oxidant gas feed with a fuel gas. At least a portion of the oxygen-depleted nonpermeate gas can be cooled by indirect heat transfer with one or more gas streams selected from the group consisting of the oxygen-containing oxidant gas feed, the reactant gas feed, and the partially reformed intermediate gas.

If a final product rich in hydrogen is desired, at least a portion of the carbon monoxide in the raw synthesis gas product can be converted to hydrogen and carbon dioxide by contacting the raw synthesis gas with a shift catalyst.

In one embodiment of the invention, the catalytic reforming reaction zone comprises at least one catalytic reforming reactor which is operated adiabatically. The oxygen-containing oxidant gas feed can comprise a gas selected from the group consisting of air and a flue gas produced by combusting a fuel in excess air. At least a portion of the heat for heating the oxygen-containing oxidant gas feed can be provided by direct combustion of a portion of the oxidant gas feed with a fuel gas. If required, one or more additional reactants selected from the group consisting of steam and carbon dioxide can be added to the partially reformed intermediate gas.

In an alternative embodiment of the invention, the catalytic reforming reaction zone comprises a heat exchanged catalytic reforming reactor wherein heat is provided within the reactor by indirect heat exchange with at least a portion of the raw synthesis gas product. At least a portion of the oxygen-depleted nonpermeate gas can be cooled by indirect heat transfer with one or more gas streams selected from the group consisting of the oxygen-containing oxidant gas feed and the reactant gas feed. The oxygen-containing oxidant gas feed can comprise a gas selected from the group consisting of air and a flue gas produced by combusting a fuel in excess air. At least a portion of the heat for heating the oxygen-containing oxidant gas feed can be provided by direct combustion of a portion of the oxidant gas feed with a fuel gas. If desired, one or more additional reactants selected from the group consisting of steam and carbon dioxide are added to the partially reformed intermediate gas.

In another alternative embodiment, the catalytic reforming reaction zone comprises a fuel-fired catalytic reforming reactor wherein heat is provided within the reactor by indirect heat exchange with combustion products formed by the combustion of a fuel and an oxygen-containing reformer combustion gas, and wherein a reforming reactor flue gas is withdrawn therefrom. At least a portion of the oxygen-depleted nonpermeate gas can be cooled by indirect heat transfer with one or more gas streams selected from the group consisting of the oxygen-containing oxidant gas feed, the oxygen-containing reformer combustion gas, and the reactant gas feed. At least a portion of the reforming reactor flue gas can be cooled by indirect heat transfer with one or more gas streams selected from the group consisting of the oxygen-containing oxidant gas feed, the oxygen-containing reformer combustion gas, and the reactant gas feed. In addition, if desired, at least a portion of the heat for heating the oxygen-containing oxidant gas feed can be provided by direct combustion of a portion of the oxidant gas feed with a fuel gas. The oxygen-containing oxidant gas feed can comprise a gas selected from the group consisting of air and a flue gas produced by combusting a fuel in excess air.

Optionally, carbon dioxide can be added to the reactant gas feed. If desired, one or more additional reactants selected from the group consisting of steam and carbon dioxide can be added to the partially reformed intermediate gas.

At least a portion of the oxygen-containing reformer oxidant gas can be provided by at least a portion of the oxygen-depleted nonpermeate gas. If desired, at least a portion of the heated oxidant gas feed into the oxidant side of the mixed conducting membrane reactor can be provided by at least a portion of the reforming reactor flue gas. A stream of air can be introduced into the heated oxidant gas feed prior to the oxidant side of the mixed conducting membrane reactor, wherein the stream of air is at a temperature below the temperature of the heated oxidant gas feed. The reactant side of the mixed conducting membrane reactor can contain a reforming catalyst to promote the reforming reactions occurring therein.

The liquid product obtained by conversion of the synthesis gas product may contain one or more components selected from the group consisting of hydrocarbons containing greater than four carbon atoms, methanol, and dimethyl ether.

DETAILED DESCRIPTION OF THE INVENTION

Figure 1:
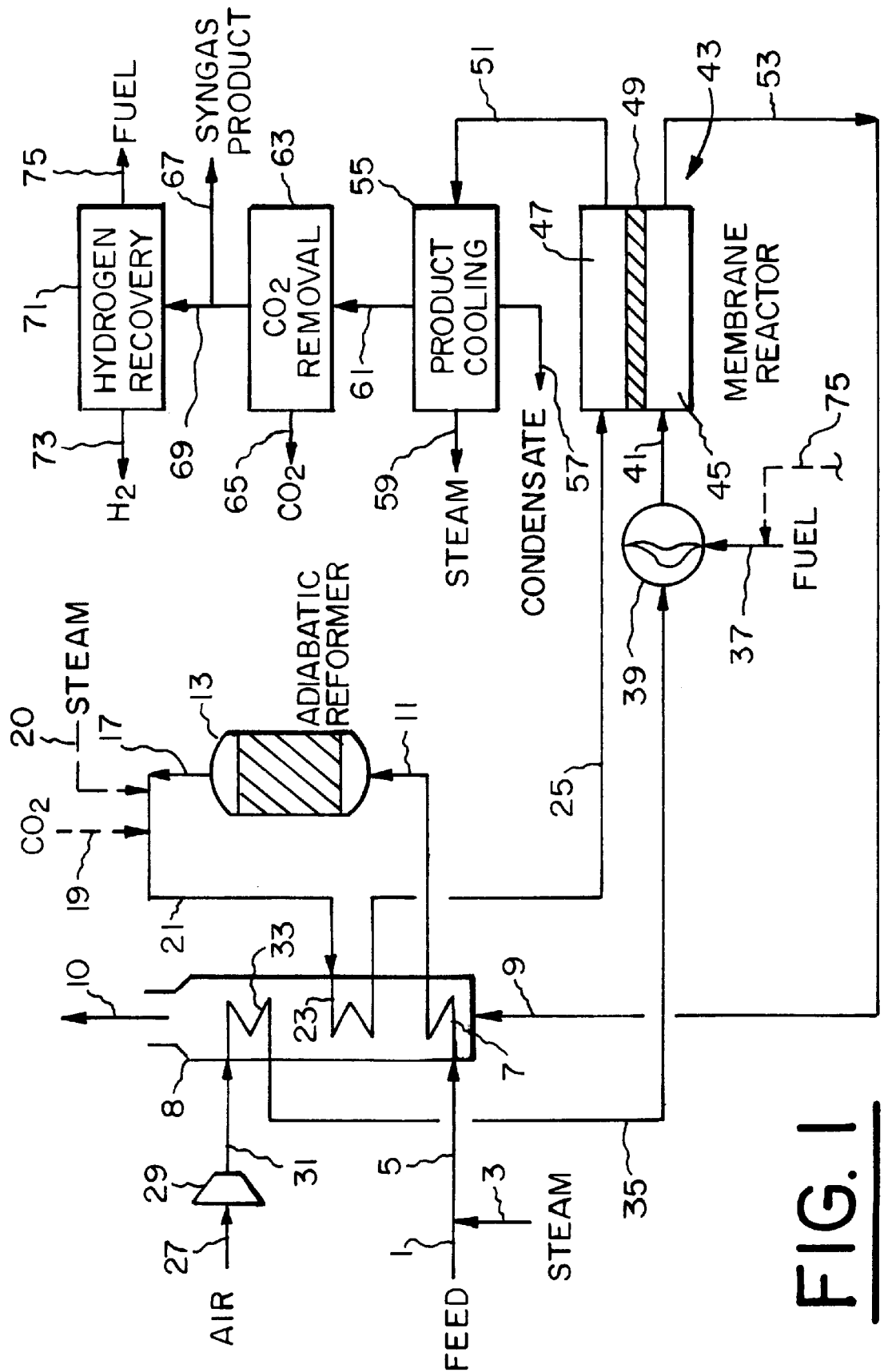
FIG. 1 is a schematic flow diagram of one embodiment of the present invention which utilizes an adiabatic reformer in combination with a mixed conducting membrane reactor.

The objective of the present invention is the production of synthesis gas using high temperature mixed conducting membrane reactors using widely available hydrocarbon feedstocks such as natural gas, associated gas from crude oil production, light hydrocarbon gases from petroleum refineries, and medium molecular weight hydrocarbons such as naphtha. The invention defines processes and methods of operation for mixed conducting membrane reactors for the production of synthesis gas by the controlled reaction of hydrocarbons with oxygen wherein the oxygen is provided in situ by permeation from an oxygen-containing gas through the mixed conducting membrane. The reactor module is integrated with specific process steps for the supply of the reactant gas feed and process steps for the withdrawal and further treatment of the reactor effluent streams. Preferred operating conditions are defined for feed gas and product gas temperatures, the pressure differential across the membrane in the reactor module, and the membrane reactor feed gas composition. The invention defines important operating conditions which have not been addressed or considered in the prior art of high temperature mixed conducting membrane reactors.

There is a significant problem not previously recognized in the operation of mixed conducting membrane reactors utilizing the hydrocarbon feedstocks mentioned above, namely, that the desired operating temperatures of mixed conducting membrane reactors could be substantially higher than the decomposition temperatures of these hydrocarbon feedstocks. Depending on the oxygen transport properties and thickness of the active membrane material, mixed conducting membranes may require temperatures substantially above about 1200° F. (649° C.) in order to achieve satisfactory oxygen permeation rates. However, these feedstocks are susceptible to cracking and carbon deposition if heated to such temperatures. For example, natural gas-steam mixtures are not heated to temperatures above about 1022° F. in commercial practice because of carbon deposition concerns, particularly at the hotter wall of the heating coil/exchanger. For a feedstock containing primarily $C_2$ to $C_5$ hydrocarbons, typically available in a petroleum refinery, cracking and carbon deposition will occur at lower temperatures. For a feedstock such as naphtha, which contains heavier hydrocarbons than those contained in natural gas or light refinery gases, this will occur at still lower temperatures.

The present invention alleviates this problem by converting such hydrocarbon feedstocks into synthesis gas in a staged process in which the components in the feed are partially reformed in an initial steam reforming step followed by final conversion to synthesis gas in a mixed conducting membrane reactor. Unlike the heavier hydrocarbons present in natural gas, methane is a relatively stable molecule and is much less prone to thermal decomposition to form elemental carbon. The steam reforming step converts essentially all of the hydrocarbons heavier than methane into methane, hydrogen, and carbon oxides and converts a portion of the methane into synthesis gas. The steam reforming step thus produces an intermediate feed stream containing methane, hydrogen, carbon oxides, and steam which can be processed without operating problems in a mixed conducting membrane reactor.

Synthesis gas production with mixed conducting membranes is generally an autothermal reforming process. The hydrocarbon feedstock is converted into synthesis gas components in part by endothermic reforming reactions and in part by exothermic partial oxidation reactions. The amount of oxygen permeation through the membrane is controlled such that the relative proportions of hydrocarbon conversion accomplished by the two sets of reactions cause the reactor to be in thermal balance. However, oxygen is also a reactant that is consumed to form CO, $CO_2$, and $H_2O$.

The amount of oxygen permeated through the membrane has two desirable effects on the overall process. The first is a thermal effect which enables the process to operate in thermal balance as implied by the term "autothermal". The second is a stoichiometric effect which determines the relative proportions of $H_2$, CO and $CO_2$ in the synthesis gas, preferably such that the synthesis gas product composition matches the operating requirements of any downstream process which consumes the synthesis gas.

In general, the operation of a mixed conducting membrane reactor without a prior reforming step would not yield both of the above desirable effects. The first desirable effect would be achieved at the expense of the second—the synthesis gas product would contain an excess of one or two components, with substantial economic penalty. The initial reforming step of the present invention affords an extra degree of freedom in the production of synthesis gas. By carrying out some endothermic reforming in this initial reforming step, the oxygen demand in the membrane reactor can be reduced to an optimum level.

The steam reforming and mixed conducting membrane reactors can be heat-integrated for maximum operating efficiency and can produce synthesis gas with optimum compositions for a variety of final products.

A number of chemical reactions occur among the chemical species present in reforming and partial oxidation reaction systems, which species can include oxygen, hydrogen, water, carbon monoxide, carbon dioxide, methane, heavier hydrocarbons, and elemental carbon. Some of the more important reactions are as follows:

$$CH_4 + \tfrac{1}{2}O_2 \rightleftharpoons 2H_2 + CO \tag{1}$$

$$CH_4 + \tfrac{3}{2}O_2 \rightleftharpoons 2H_2O + CO \tag{2}$$

$$CH_4 + 2O_2 \rightleftharpoons 2H_2O + CO_2 \tag{3}$$

$$CH_4 + H_2O \rightleftharpoons 3H_2 + CO \tag{4}$$

$$CH_4 + CO_2 \rightleftharpoons 2H_2 + 2CO \tag{5}$$

$$CO + H_2O \rightleftharpoons H_2 + CO_2 \tag{6}$$

$$H_2 + CO \rightleftharpoons C + H_2O \tag{7}$$

$$2CO \rightleftharpoons C + CO_2 \tag{8}$$

$$C_nH_m \rightleftharpoons nC + m/2\,H_2 \tag{9}$$

$$C_nH_m + nH_2O \rightleftharpoons nCO + (n+m/2)\,H_2 \tag{10}$$

$$C_nH_m + nCO_2 \rightleftharpoons 2nCO + (m/2)\,H_2 \tag{11}$$

Reactions similar to oxidation reactions (1), (2), (3) above also can occur with heavier hydrocarbons as well under the proper conditions. Reaction (9) is a simple stoichiometric representation of several parallel, complex reaction sequences, including the formation of olefins and their polymerization into carbon.

An objective of the present invention is to produce synthesis gas from feedstocks which contain significant amounts of hydrocarbons heavier than methane while utilizing the advantages of mixed conducting membrane reactors for the autothermal reforming of methane to hydrogen and carbon monoxide. The preferred embodiments of the present invention as described below are utilized to ensure that only reactions (1) through (6) above occur in the mixed conducting membrane reactor, although reactions (4) through (6) also may occur to some extent in the feed reforming reactor, and that reactions (10) and (11) occur in the feed reforming reactor so that reaction (9) does not occur in the equipment and manifolds preceding the mixed conducting membrane reactor and within the reactor itself. It is also desirable to control conditions within and downstream of the mixed conducting membrane reactor so that reactions (7) and (8) do not occur.

A first embodiment of the present invention is illustrated in FIG. 1. Reactant gas feed 1 typically is a preheated and appropriately pretreated natural gas with a typical composition in the range of at least 80 vol % methane, less than 10 vol % $H_2$, less than 20 vol % ethane, less than 10 vol % propane, less than 5 vol % alkanes with more than 3 carbon atoms, less than 10 vol % carbon dioxide, less than 10 vol % nitrogen, less than 50 parts per billion (ppb) total sulfur, and no olefins. Alternatively, reactant gas feed 1 can be a preheated and appropriately pretreated methane-containing gas from a petroleum refinery, petrochemical plant, or other industrial source. Reactant gas feed 1 can be obtained by the prior treatment of natural gas at an elevated temperature (500 to 800° F., 260 to 427° C.) with hydrogen in a catalytic hydrogenation reactor to convert any olefins present into paraffins and any organic sulfur present into hydrogen sulfide (not shown). The hydrogen sulfide is removed by a sulfur sorbent such as zinc oxide (not shown). These hydrogenation and desulfurization steps are well known in the steam reforming art and are utilized to ensure that no olefin cracking and catalyst poisoning by sulfur occur in downstream processing equipment.

Alternative feedstocks for providing reactant feed gas 1 include lower molecular weight hydrocarbon fractions such as liquefied petroleum gas (LPG) or intermediate molecular weight hydrocarbon fractions such as naphtha. These alternative feedstocks can be vaporized, desulfurized, and freed of olefins by known methods referenced above.

Reactant gas feed 1 typically is provided at pressure of about 10 to 900 psig (0.69 to 62.1 barg), preferably 200 to 400 psig (13.8 to 27.6 barg), by compression, pressure reduction, or pumping and vaporization of the feedstock prior to pretreatment. Depending on the degree and type of pretreatment used for sulfur and olefin removal, reactant gas feed 1 can be at a temperature between ambient temperature and about 800° F. (427° C.). Steam 3 is introduced into feed 1 to provide steam-hydrocarbon feed 5 having a steam to carbon molar ratio of about 0.3 to 5. Either or both of steam 3 and feed 1 has been sufficiently preheated (not shown), typically by heat exchange with a suitable hot effluent stream in the process, so that a mixture of these streams is above its dew point as described below. Preferably the steam to carbon molar ratio (defined as the moles of steam divided by the total moles of hydrocarbon compounds expressed as carbon) is in the range of about 0.3 to about 5.0.

Steam-hydrocarbon feed 5 is heated in heat exchanger 7 in heat exchange zone 8 against hot process gas stream 9 (later defined) to a temperature of 700 to 1022° F. (372 to 550° C.) and heated feed 11 is introduced into adiabatic reformer reactor 13. Adiabatic reformer reactor 13 is a packed-bed reactor containing a highly-active, relatively low-temperature reforming catalyst such as the well-known British Gas CRG-F catalyst manufactured under license by ICI Katalco. The reforming reactions of steam and hydrocarbons occur in adiabatic reformer reactor 13 via reactions (4), (6), and (10) presented earlier.

If reactant gas feed 1 resulted from a typical natural gas, the overall process will be endothermic, and partially reformed intermediate gas 17 from adiabatic reformer reactor 13 will be about 50 to 300° F. (28 to 149° C.) cooler than heated feed 11. If reactant gas feed 1 is prepared from a mixture of heavier hydrocarbons such as naphtha, the overall process will be exothermic, and partially reformed intermediate gas 17 from adiabatic reformer reactor 13 will be hotter than heated feed 11. If reactant gas feed 1 is a mixture of lighter hydrocarbons such as propane and butane, the overall process can be approximately heat-neutral, and partially reformed intermediate gas 17 from adiabatic reformer reactor 13 will be at about the same temperature as heated feed 11.

Partially reformed intermediate gas as used herein is defined as the product gas formed by the reaction of steam with a feed gas containing one or more hydrocarbons heavier than methane, and optionally containing methane, wherein the reaction products comprise methane, carbon oxides, hydrogen, and steam (defined herein as vaporized or gaseous water). The partially reformed intermediate gas preferably is essentially free of hydrocarbons heavier than methane, which means that this gas contains less than about 100 ppm by volume of hydrocarbons heavier than methane.

In adiabatic reformer reactor 13, essentially all hydrocarbons heavier than methane are converted into hydrogen, carbon oxides, methane, and steam; if methane is present in the feed, some of the methane may be converted as well into hydrogen and carbon oxides. Partially reformed intermediate gas 17 optionally is combined with carbon dioxide stream 19 and optionally with steam stream 20, and the combined stream 21 can be further heated if necessary in heat exchanger 23 in heat exchange zone 8 to yield heated partially reformed intermediate gas 25 at 1100 to 1400° F. (594 to 760° C.). Partially reformed intermediate gas 17 is typically within a 50° F. temperature approach to reforming and shift-equilibrium and its composition can be calculated from published values of the reaction equilibrium constants for the reforming and shift reactions—the main stipulation is that all hydrocarbons heavier than methane are quantitatively converted essentially to extinction.

In an optional version of the present embodiment, a second stage adiabatic reformer reactor can be used (not shown) wherein reheated partially reformed intermediate gas 25 is introduced directly into the second reactor where further reforming occurs. The further reformed effluent gas is reheated in heat exchange zone 8.

Oxygen-containing gas 27, preferably air, is pressurized in compressor or blower 29 to a pressure in the range of about 1 to about 900 psig (0.069 to 62.1 barg), preferably less than about 10 psig (0.69 barg). While air is the preferred oxygen-containing gas, other oxygen-containing gases can be utilized as an oxygen source for the process as described later. Pressurized oxygen-containing gas 31 is preheated in heat exchanger 33 in heat exchange zone 8, and preheated oxygen-containing gas 35 is heated further if necessary by direct combustion with fuel 37 in burner 39 to yield heated oxidant 41 typically containing 15 to 21 vol % oxygen at a temperature preferably within ±200° F. (±111° C.) of the temperature of partially reformed intermediate gas 25. Burner 39 represents any type of known, commercially-available combustion device for promoting essentially complete combustion of fuel 37 in an excess oxygen environment, and the heating of oxygen-containing gas 35 in this manner is defined as heating by direct combustion. Fuel 37 can include purge gases from downstream synthesis gas consuming unit operations, supplemented by natural gas for startup or control. Preferably, fuel 75 from hydrogen recovery system 71 is used as part of fuel 37.

The term oxygen is used herein to describe generically any form of oxygen (O, atomic number 8) present in the gas streams and reactor systems described. The generic term oxygen includes dioxygen ($O_2$), oxygen ions (for example $O^-$ or $O^=$), atomic oxygen (O•), or other forms of oxygen derived from dioxygen in the gas streams and systems described. The term oxygen ion means any form of charged oxygen. The term oxygen as used herein does not include oxygen which is chemically bound in carbon oxides, nitrogen oxides, or other oxygen-containing compounds.

Heated oxidant 41 and heated partially reformed intermediate gas 25 are introduced into respective oxidant and reactant inlets to mixed conducting membrane reactor 43. Heated oxidant 41 is at a temperature preferably within ±200° F. of the temperature of heated partially reformed intermediate gas 25 at the inlet to mixed conducting membrane reactor 43. The gas temperature at the reactant inlet is in the range of about 1100 to 1400° F. (594 to 760° C.).

Mixed conducting membrane reactor 43 is shown schematically having oxidant side 45 separated from reactant side 47 by mixed conducting membrane 49 and is presented in this simplified format for the following description of the reactor operation. Oxidant side 45 represents a reactor volume through which the oxidant gas flows and contacts the oxidant side surface of mixed conducting membrane 49. Dioxygen is ionized at this surface to form oxygen ions and the oxygen ions permeate mixed conducting membrane 49 to the reactant side surface of the membrane.

The term mixed conducting membrane as used herein defines a solid material or mixture of solid materials which simultaneously conducts both charged oxygen species (for example oxygen ions) and electronic species (for example electrons). The mixed conducting membrane can comprise any solid material or materials known in the art which perform these simultaneous functions. Such materials are described for example in the earlier-cited U.S. Pat. No. 5,306,411 and in a paper entitled "Electropox Gas Reforming" by T. J. Mazanec in *Electrochem. Soc. Proceedings* 95–24, 16(1997).

Alternatively, the mixed conducting membrane can be a mixture of one or more ion conducting solid materials and one or more solid materials which conduct electronic species (such as electrons) wherein the mixture of solid materials forms a composite mixed conducting membrane. One example of a composite mixed conducting membrane uses zirconia as the charged oxygen species conducting solid material and palladium as the conductor of electronic species. Another example of a composite mixed conducting membrane uses zirconia as the charged oxygen species conducting solid material and a mixture of indium and praseodymium oxides as the conductor of electronic species.

The term mixed conducting membrane as defined above is included in the generic class of membranes which has been described in the art by the term ion transport membrane. In the present disclosure, the term mixed conducting membrane is used in the context of the above definitions.

The active mixed conducting membrane material in mixed conducting membrane 49 can be a thin layer on a planar or tubular porous support as is known in the art. The support may be fabricated from an inert material which does not conduct oxygen ions and/or electronic species at process operating conditions. Alternatively the support can be an ionically conducting material, an electronic species conducting material or a mixed conducting oxide material of the same or different composition than the active layer of mixed conducting membrane material. Preferably, the porous support is fabricated from a material having thermal expansion properties which are compatible with the mixed conducting membrane material, and the compositions making up the respective layers should be selected from materials which do not adversely chemically react with one another under process operating conditions.

The surface of mixed conducting membrane 49 in oxidizing side 45 optionally can be coated with catalytic material to promote the transfer of oxygen into the membrane. Such materials are known in the art and include metals and oxides of metals selected from Groups 2, 5, 6, 7, 8, 9, 10, 11, 13, 14, 15 and the F Block lanthanides of the Periodic Table of the Elements according to the International Union of Pure and Applied Chemistry. Suitable metals include platinum, palladium, ruthenium, silver, bismuth, barium, vanadium, molybdenum, cerium, praseodymium, cobalt, rhodium and manganese.

Reactant side 47 represents a reactor volume through which partially reformed intermediate gas 25, also described herein as reactant gas 25, flows and reacts with oxygen which has permeated through mixed conducting membrane 49. A number of chemical reactions occur in reactant side 47 among the several chemical species present including oxygen, hydrogen, water, carbon monoxide, carbon dioxide, methane, and possibly elemental carbon. These primary reactions (1) to (8) have been earlier described.

These reactions are similar to the known reactions which occur in the conventional autothermal reforming of methane to product synthesis gas. Oxidation reactions (1), (2), and (3) are shown as consuming dioxygen, which may occur in reactant side 47 of membrane reactor 43. In addition, other forms of oxygen as earlier described may react with methane, CO, and $H_2$ to form $H_2O$, CO, $CO_2$, and $H_2$. The exact reaction mechanisms between permeated oxygen and hydrocarbons in reactant side 47 are not fully understood, but at least carbon monoxide and hydrogen are net formed as final reaction products. Reactions (1), (2), (3), and (6) are exothermic while reactions (4) and (5) are endothermic; the exothermic reactions (2) and (3) are kinetically very fast, require some form of oxygen, and can occur without any catalyst; while the endothermic reactions (4) and (5) are slower, and benefit from the reforming catalyst.

Reactions (7), (8), and (9) form elemental carbon which is undesirable in reactor operation. The deposition of carbon, also known as coking, can cause serious problems at the reactor inlet, within the reactor, and in outlet lines downstream of the reactor. Reaction (9) is known as hydrocarbon cracking, particularly the cracking of the higher hydrocarbons such as ethane, propane, and butane which are present in natural gas at low but significant concentrations. Cracking is favored by high temperatures, and can occur over hot metallic surfaces, nickel catalyst sites, and acidic sites on refractory materials such as catalyst supports. The reactant inlet piping and the feed region of membrane reactor 43 are particularly vulnerable to carbon deposition by this mechanism if heavier hydrocarbons are present in reactant feed 25. The extent of carbon deposition by reaction (9) is determined by the reactant feed temperature, composition, and pressure.

As earlier described, essentially all hydrocarbons heavier than methane are converted in adiabatic reformer reactor 13, and carbon deposition by reaction (9) will be negligible since methane itself is much more stable relative to the heavier hydrocarbons present in natural gas. A mixture of natural gas and steam would typically be limited to a preheat temperature of about 1022° F. (550° C.). A mixture containing methane, steam, hydrogen, CO, and $CO_2$, but no hydrocarbons heavier than methane, i.e. partially reformed intermediate gas 25, can be heated to higher temperatures, even above 1200° F. (649° C.).

A desirable feature of the present invention is that reactant gas 25 can be preheated to a temperature above 1200° F. (649° C.) prior to membrane reactor 43, at which temperature there is sufficient oxygen flux allowing the reactant gas temperature within reactant side 47 to increase rapidly to the preferred temperature range above 1500° F. (816° C.) as exothermic reactions occur therein.

The total gas pressure at any point in reactant side 47 is about 1 to 900 psig (0.069 to 62.1 barg), preferably 200 to 400 psig (13.8 to 22.6 barg), and a small pressure drop occurs from the inlet to the outlet. The total gas pressure at any point in oxidant side 45 should be in the range of about 1 to about 900 psig (0.069 to 62.1 barg), preferably less than about 10 psig (0.69 barg); the pressure decreases slightly from the inlet to the outlet. It is preferred but not required that the total pressure at any point in reactant side 47 of the reaction zone 43 is greater than the total pressure at any point in oxidant side 45.

In the reactions discussed above, one mole of methane yields close to one mole of carbon monoxide which is contained in about 3 moles of synthesis gas, which is withdrawn at approximately the pressure of reactant side 47 of membrane reactor 43. The partial oxidation process typically requires about 0.6 moles of oxygen per mole of methane, which needs at a minimum about 3 moles of air at 100% oxygen recovery, and substantially more at lower recovery. For feedstocks heavier than methane, each carbon atom yields close to one mole of CO which is contained in 2 to 3 moles of synthesis gas.

Air 27 is available at ambient pressure. The compressor power required for compressor or blower 29 is roughly proportional to the molar flow rate and the logarithm of the pressure ratio. The cost of the compressor is sensitive to the actual volumetric flow rate at inlet conditions—lower inlet pressures can increase the compressor size and cost, even at the same molar flow rate. Compression ratios less than about 3 generally need only a single stage of compression; higher ratios need additional stages with intercoolers.

It is preferable but not required that reactant gas feed 1 be available at a superatmospheric pressure, either by compression (if the original feed is a gas) or by liquid pumping followed by vaporization (if the original feed is a liquid) prior to the -pretreatment steps earlier discussed. Compression of product synthesis gas should be minimized or eliminated because synthesis gas is produced at approximately three times the molar flow rate of reactant gas feed 1. Compressing air 27 to a high pressure is the least desirable option since air is required at the highest flow rate and is available at ambient pressure.

Thus the membrane reactor preferably is designed to operate with the maximum pressure differential between the reactant side and the oxidant side subject to reasonable mechanical and fabrication constraints. The oxidant side should be operated as close to ambient pressure as possible sufficient to overcome the total system pressure drop, the membrane reactor should be designed to minimize the pressure drop therein, and fan or blower 29 preferably is used to supply air 31 to the reactor oxidant preparation system.

As the oxidant and reactant gases flow through membrane reactor 43, oxygen permeates through mixed conducting membrane 49 and reactions (1) through (6) proceed in reactant side 47 to yield the desired synthesis gas product. Preferably a reforming catalyst is applied to at least a portion of the reactant side surface of mixed conducting membrane 49 to promote the desired reactions. Alternatively or additionally, reforming catalyst in granular or pellet form can be packed into reactant side 47 adjacent to the surface of mixed conducting membrane 49. Catalysts for this purpose are well known in the art.

Raw synthesis gas product 51 is withdrawn at the outlet of reactant side 47 of membrane reactor 43 at a temperature of greater than about 1500° F. (816° C.) and contains hydrogen and carbon monoxide with a hydrogen to carbon monoxide molar ratio of 1 to 6. There is negligible dioxygen ($O_2$), and the gas is within a 50° F. approach to reforming and shift equilibrium so that the $H_2$, CO, $CO_2$, $CH_4$ and $H_2O$ content can be calculated from the published values of the equilibrium constants for the reforming and shift reactions as a function of temperature.

Oxygen-depleted non-permeate 53 is withdrawn from oxidant side 45 at a temperature at or slightly below that of raw synthesis gas product 51. With oxidant and reactant in cocurrent flow through the membrane reactor, the temperature of non-permeate 53 can approach to within 9 to 180° F. (5 to 100° C.) of the temperature of raw synthesis gas product 51. The temperature rises in a controlled manner from the inlet to the outlet of membrane reactor 43 because the combination of individual endothermic and exothermic reactions which occur therein are net exothermic as earlier described.

Preferably at least about 90% of the oxygen in heated oxidant 41 permeates mixed conducting membrane 49, so that oxygen-depleted non-permeate 53 preferably contains less than about 2 vol % oxygen. A high oxygen recovery will minimize the power requirements of compressor or blower 29 because a minimum volume of gas is compressed.

Oxygen-depleted non-permeate 53 provides hot process gas stream 9 to heat exchange zone 8 as earlier described. Heat exchange zone 8 is essentially a conventional flue gas duct as used in steam-methane reforming furnaces which is laced with various heat exchanger coils for heating the appropriate process streams as described herein. A major portion of the heat content of oxygen-depleted non-permeate 53 is transferred via heat exchangers 7, 23, and 33 to heat process streams as earlier described, and also to preheat and vaporize raw feedstocks and/or to superheat steam as earlier suggested. The flue gas side of this heat exchange duct generally operates at a pressure drop of 12 to 30 inches of water and discharges final flue gas 10 to the atmosphere. An induced draft fan (not shown) can be used to discharge the exhaust steam 10 into the atmosphere. Final flue gas 10 is rejected at a temperature at least 100° F. above its dew point.

Mixed conducting membrane reactor 43 as described above is presented in a simplified format for explanation of the membrane reactor process features. In actual practice, mixed conducting membrane reactor 43 comprises one or more reactor modules, each of which contains multiple membranes with multiple oxidant and reactant channels or cells wherein a single reaction cell is characterized by oxidant side 45, reactant side 47, and mixed conducting membrane 49 of FIG. 1. Numerous designs of membrane reactor modules for this purpose have been described in the art as summarized in the background information presented above, and these designs include both cocurrent flow and crossflow modules utilizing tubular, corrugated plate, and monolith configurations.

As raw synthesis gas product 51 from membrane reactor 43 cools in downstream equipment, it will enter a temperature range where carbon deposition by the reaction (8), known as the Boudouard reaction, is favored; the exact temperature depends primarily on the partial pressures of carbon monoxide and carbon dioxide in the stream. The carbon causes severe erosion by corrosion of metallic surfaces of downstream heat transfer equipment, particularly in high temperature metal alloys which contain nickel; this is a phenomenon widely referred to as "metal dusting". Metal dusting is kinetically inhibited below a temperature of about 800° F. (427° C.). Thus metal dusting can be avoided by maintaining all metallic surfaces downstream of the reactor at temperatures below 800° F. (427° C.). A process waste heat boiler accomplishes this by maintaining the temperature of the metal tubes close to the temperature of the boiling water. The heat flux and vapor fraction in the boiling water are limited such that high condensing heat transfer coefficients are obtained. Another approach is to quench the synthesis gas effluent 49 with a stream of warm water to below 800° F. (427° C.) prior to any heat exchange.

Raw synthesis gas product 51 is cooled rapidly (quenched) to a temperature below 800° F. (427° C.) against boiling water by indirect heat transfer in product cooling zone 55 and can be further cooled therein against other process streams. Water 57 which is condensed from raw synthesis gas product 51 and steam 59 which is generated by cooling raw synthesis gas product 51 are withdrawn for further use. Depending on the end use of the synthesis gas, some or all of cooled and dewatered synthesis gas 61 can be treated in carbon dioxide removal system 63 using known methods to remove some or all of the carbon dioxide contained in the raw synthesis gas. Recovered carbon dioxide 65 is withdrawn from the system, and optionally a portion can be used to provide carbon dioxide 19 for combination with partially reformed intermediate gas 17. If only a portion of cooled and dewatered synthesis gas 61 is treated in carbon dioxide removal system 63, the remaining untreated portion is combined with the treated portion (not shown) to yield final synthesis gas or syngas product 67.

Final synthesis gas product 67 is withdrawn from the system, compressed if required (not shown), and utilized for final product synthesis. A portion 69 of the final synthesis gas product can be separated in hydrogen recovery system 71, typically a pressure swing adsorption (PSA) system, to yield hydrogen 73 and fuel gas 75 for use elsewhere in the process. Hydrogen 73 typically is used for the pretreatment of reactant feed 1 as earlier described. Alternatively, a portion of cooled and dewatered synthesis gas 61 can be treated in hydrogen recovery system 71 to yield hydrogen 73.

Figure 2:
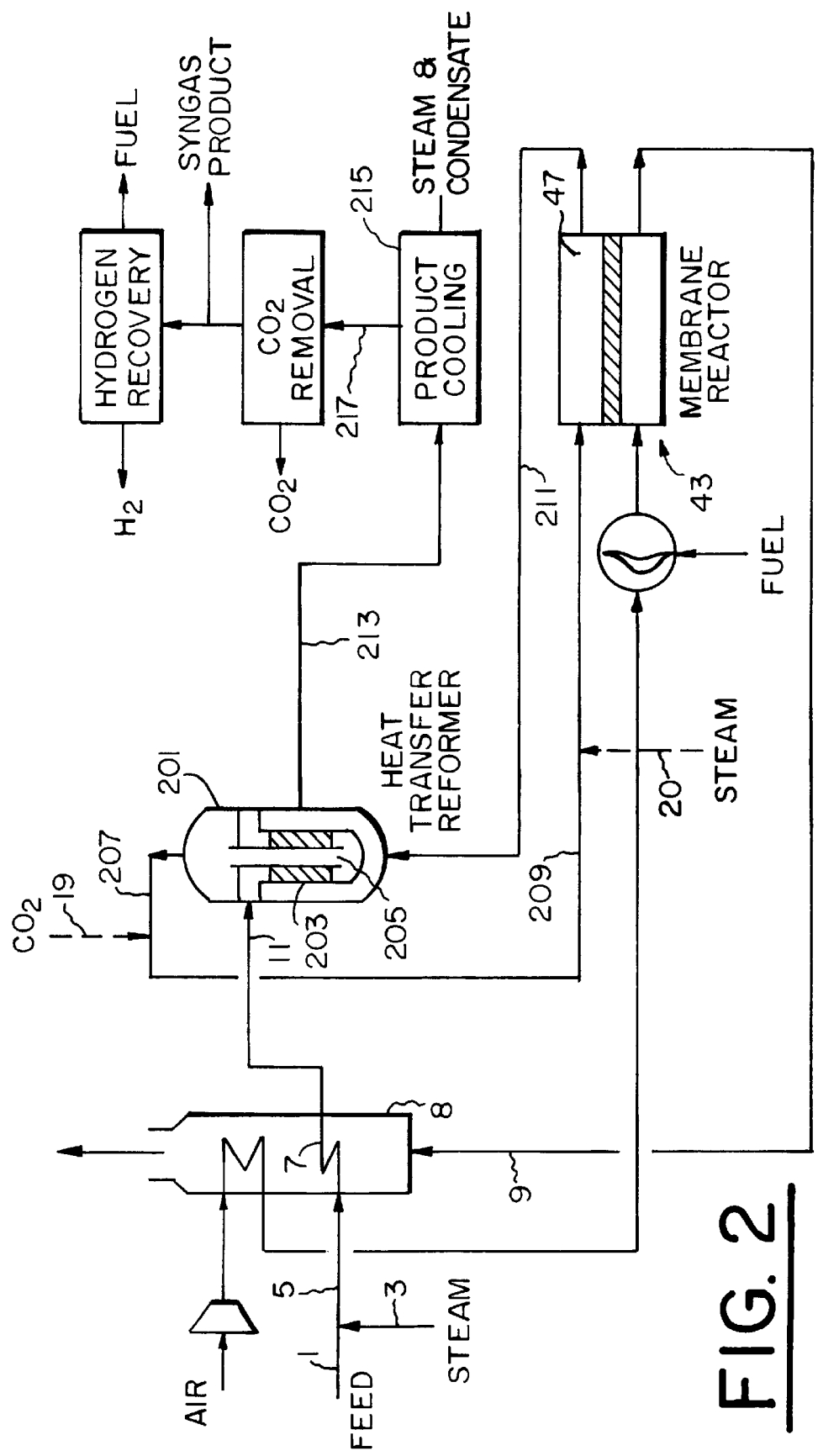
FIG. 2 is a schematic flow diagram of a second embodiment of the present invention which utilizes a gas heated reformer in combination with a mixed conducting membrane reactor.

Another embodiment of the invention is illustrated in FIG. 2. In this embodiment, a different type of reformer, a special kind of heat transfer reformer described in the art by the commercial term gas heated reformer (GHR), is used for the partial reforming of reactant feed gas 1. This type of reactor also is described herein as a heat exchanged catalytic reforming reactor. As described in the embodiment of FIG. 1, preheated and pretreated feed 1 is mixed with steam 3 to provide steam-hydrocarbon feed 5 having a steam to carbon molar ratio of about 2.5 to 5. Steam-hydrocarbon feed 5 is heated in heat exchanger 7 in heat exchange zone 8 against hot process gas stream 9 (earlier defined) to a temperature of 700° F. to 1022° F. (372° C. to 550° C.) to provide heated feed 11.

Heated feed 11 is introduced into heat transfer reformer 201 which contains reforming catalyst in tubes or annular channels which are disposed in an indirect exchange heat relationship with a separate hot gas stream which provides the heat required for endothermic reforming reactions occurring on the catalyst side of the tubes or channels. A nickel-based steam reforming catalyst such as ICI Katalco 57-4M can be used. This type of reformer reactor is useful when reactant feed gas 1 is preheated and pretreated natural gas. One commercially available type of heat transfer reformer which is particularly suitable in the process of the present invention is the ICI gas-heated reformer described in the earlier cited paper by K. J. Elkins et al entitled "The ICI Gas-Heated Reformer (GHR) System" presented at Nitrogen '91 International Conference, Copenhagen, June 1991.

Heated feed 11 is introduced into heat transfer reformer 201, passes through reforming catalyst 203 to convert all hydrocarbons heavier than methane. Some of the methane also is reformed as the temperature of the gas rises. The reaction product flows through center tube 205, which is insulated from reforming catalyst 203 in the annular volume as shown, and is withdrawn as partially reformed intermediate gas 207. Partially reformed intermediate gas 207 contains the same components as partially reformed intermediate gas 17 of FIG. 1, but can be at a higher temperature and its composition can be calculated in exactly the same way as described earlier with respect to FIG. 1. However, the temperature approach to reforming equilibrium may be higher in a gas heated reformer than in an adiabatic reformer. Carbon dioxide 19 optionally is added to partially reformed intermediate gas 207 to yield reactant feed gas 209 to membrane reactor 43. Steam 20 can be added if required. Membrane reactor 43 operates as described above in the embodiment of FIG. 1.

A desirable feature of the present invention is that reactant feed gas 209 can be heated further to a temperature above 1200° F. (649° C.) prior to membrane reactor 43, at which temperature there is sufficient oxygen flux allowing the reactant gas temperature within reactant side 47 to increase rapidly to the preferred temperature range above 1500° F. (816° C.) as exothermic reactions occur therein. This heating, if required, can be provided by indirect heat exchange with the process gas stream 9 in heat exchange zone 8 (not shown). If steam 20 and/or carbon dioxide 19 are added to partially reformed intermediate gas 207, the combined gas stream can be heated prior to membrane reactor 43.

Raw synthesis gas product 211 is withdrawn at the outlet of reactant side 47 of membrane reactor 43 at a temperature of greater than about 1500° F. (816° C.) and provides heat to heat transfer reformer 201 to supply the endothermic heat of reaction required by the reforming reactions occurring therein. Cooled raw synthesis gas product 213 is withdrawn therefrom and is further cooled in product cooling zone 215. Further cooled synthesis gas product 217 may be further processed for carbon dioxide removal and hydrogen recovery as described in the embodiment of FIG. 1 to yield syngas product 67.

Figure 3:
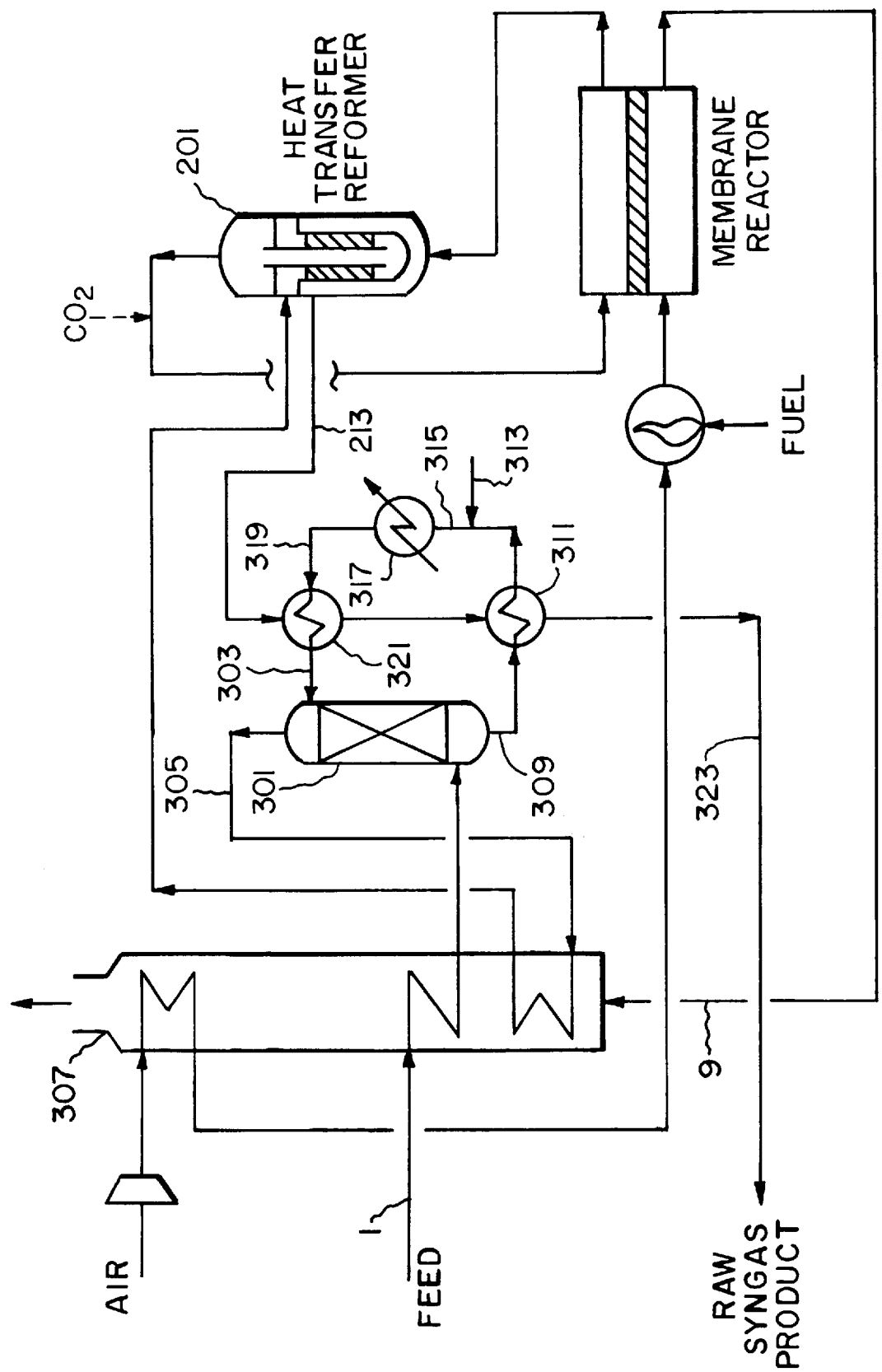
FIG. 3 is a schematic flow diagram of an alternative mode of the second embodiment of the present invention which utilizes a gas heated reformer in combination with a mixed conducting membrane reactor and saturator.

An optional method to provide reactant steam required for heat transfer reformer 201 is described in FIG. 3. In this alternative, reactant feed gas 1 is directly saturated with water vapor by saturator 301 where it is contacted with hot water 303 to achieve a water to carbon molar ratio between about 2.5 to about 5. Saturator 301 can be any type of gas-liquid contactor such as a spray tower, packed tower, or trayed column. Reactant feed gas 305, now containing vaporized water, is reheated by heat exchange with oxygen-depleted air in heat exchange zone 307 and passes to heat transfer reformer 201 where the process continues as described with reference to FIG. 3.

Water bottoms stream 309 is heated in heat exchanger 311 against a hot process stream later defined, is combined with makeup water 313, the combined water stream 315 is optionally further heated in heat exchanger 317 against any available hot process stream, and the resulting water stream 319 is further heated in heat exchanger 321 to provide hot water 303. Heat for heat exchangers 311 and 321 is provided by cooling intermediate synthesis gas product 213 to provide raw synthesis gas product 323. Raw synthesis gas product 323 is further processed as earlier described in the embodiment of FIG. 1 to yield syngas product 67 (not shown). Metal dusting in heat exchangers 311 and 321 is minimized using appropriate metal surface treatment as is known in the art.

Figure 4:
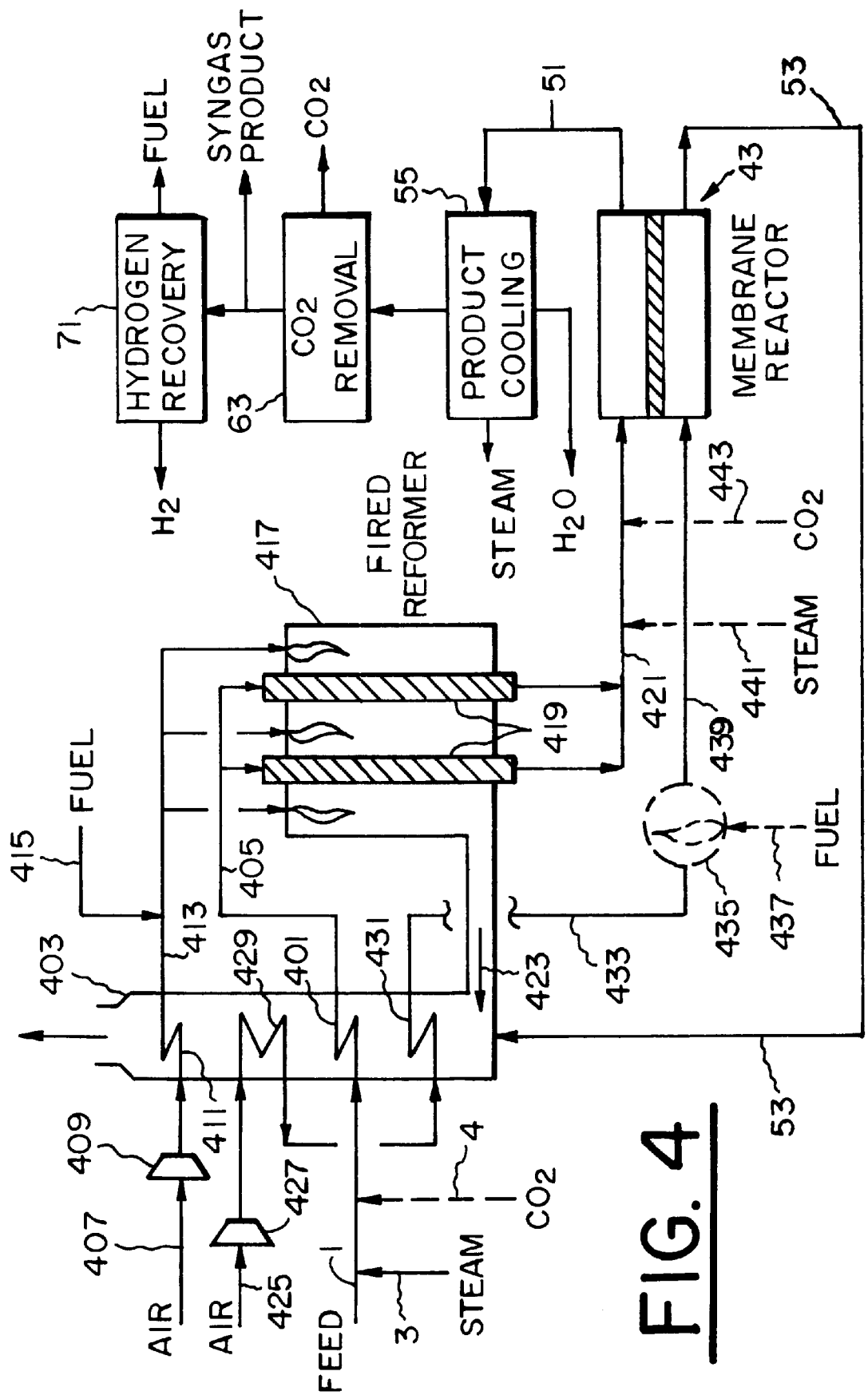
FIG. 4 is a schematic flow diagram of a third embodiment of the present invention which utilizes a fired tubular reformer in combination with a mixed conducting membrane reactor.

An alternative embodiment of the invention is illustrated in FIG. 4. Reactant feed gas 1 is combined with steam 3 and optionally with carbon dioxide 4 to yield a steam to carbon molar ratio between about 1.5 and 5.0, and the resulting combined feed gas is heated by heat exchanger 401 in heat exchange zone 403 to yield heated reformer feed 405 at 700 to 1022° F. (371 to 550° C.). Oxygen-containing gas 407 is pressurized in blower 409 to about 0.1 to 5 psig (0.007 to 0.35 barg) and heated in heat exchanger 411 in heat exchange zone 403. The resulting heated oxidant stream 413 is combusted with fuel 415 in multiple burners within fired tubular reformer 417. This type of reactor also is described herein as a fuel-fired catalytic reforming reactor. Fuel 415 can include purge gases from downstream synthesis gas consuming unit operations and/or purge gas from hydrogen recovery system 71. Syngas product 67 is recovered as in the embodiment of FIG. 1.

Heated reformer feed 405 is introduced into multiple catalyst-containing reformer tubes 419 within fired tubular reformer 417 wherein the feed is partially reformed and exits the reformer at temperatures in the range of 1200 to 1750° F. (640 to 954° C.). The reforming reactions of steam and hydrocarbons occur in reformer tubes 419 according mainly to reactions (4), (5), (6), (10) and (11) presented earlier. Intermediate synthesis gas product 421 is withdrawn at a temperature in the range of 1200 to 1750° F. (640 to 954° C.) and a pressure in the range of 1 to 850 psig (0.69 to 58.6 barg). The reformer exit pressure is dependent on the temperature, and fired tubular reformers can be operated at 500 psia (34.5 bara) at 1600° F. (871° C.). Higher operating pressures are possible at lower exit temperatures. Intermediate synthesis gas 421 will contain essentially no hydrocarbons heavier than methane and will be within a 0 to 400° F. approach to reforming and shift equilibrium. The distribution of $CO$, $CO_2$, $CH_4$, $H_2$, and $H_2O$ can be calculated using the published equilibrium constants for the reforming and shift reactions as a function of temperature.

Fired tubular reformer 417 is of any type known in the art including box side-fired, box top-fired, terrace-walled, and cylindrical reformers. Such devices are available from a number of international vendors, including KTI, Haldor-Topsoe, ICI, Howe-Baker, Foster-Wheeler, and M. W. Kellogg.

The overall reaction in reformer tubes 419 is endothermic. The required heat is provided by indirect heat transfer from combustion gases on the outside of reformer tubes 419. Flue gas 423 enters heat exchange zone 403 and provides a portion of the heat to heat exchangers located therein. Typically, an induced draft fan (not shown) exhausts the flue gas to the atmosphere and furnace 417 operates under a slight vacuum.

Oxygen-containing gas 425, preferably air, is pressurized in compressor or blower 427, preferably to less than 10 psig (0.69 barg) and heated in heat exchangers 429 and 431 in heat exchange zone 403. Heated oxygen-containing gas 433 optionally may be further heated by direct combustion in combustor 435 with fuel 437, and heated oxygen-containing gas 439 at above 1100° F. (594° C.) is introduced into membrane reactor 43. Intermediate synthesis gas product 421 optionally is combined with preheated steam 441 and/or preheated carbon dioxide 443 and introduced into membrane reactor 43. The operation of membrane reactor 43, product cooling zone 55, carbon dioxide removal system 63, and hydrogen recovery system 71 operate as described above in the embodiment of FIG. 1 to yield syngas product 67. A desirable feature of the present invention is that intermediate synthesis gas product 421 can be heated further if necessary to a temperature above 1200° F. (649° C.) prior to membrane reactor 43, at which temperature there is sufficient oxygen flux allowing the reactant gas temperature within reactant side 47 to increase rapidly to the preferred temperature range above 1500° F. (816° C.) as exothermic reactions occur therein. If steam 441 and/or carbon dioxide 443 are added to intermediate synthesis gas product 421, the combined gas stream can be heated prior to membrane reactor 43.

Oxygen-depleted non-permeate 53 is withdrawn from membrane reactor 43 at a temperature at or slightly below the temperature of raw synthesis gas product 51 and is introduced along with flue gas 423 at 1200 to 2200° F. (699 to 1206° C.) into heat exchange zone 403. The non-permeate and flue gas flowing therein provide heat for heat exchangers 401, 411, 429, and 431 described above. Heat exchange zone 403 is a conventional flue gas duct as used in steam-methane reforming furnaces which is laced with various heat exchanger coils for heating the appropriate process streams as described above. Other process streams (such as water or steam) can be heated in heat exchange zone 403 if desired.

Figure 5:
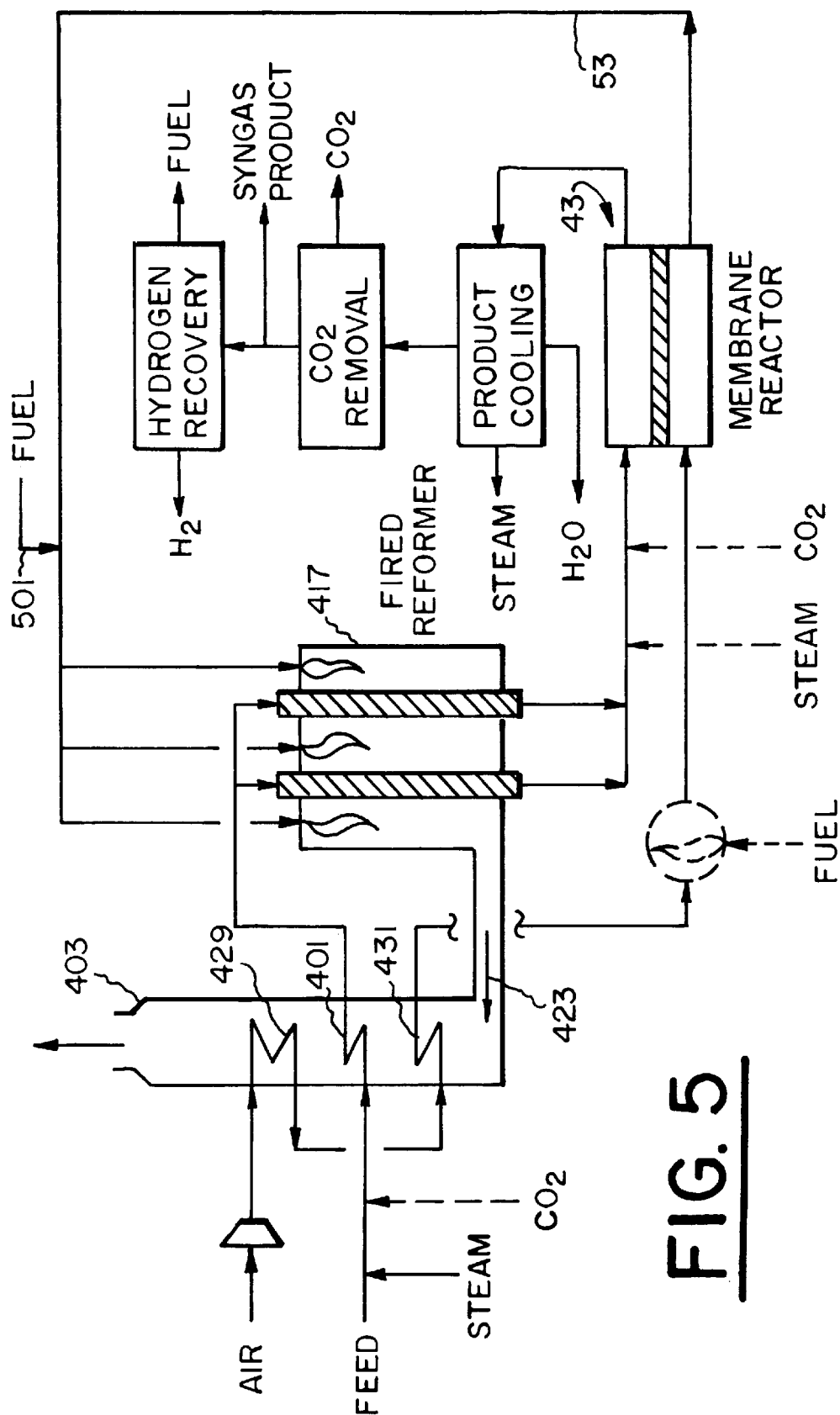
FIG. 5 is a schematic flow diagram of an alternative mode of the third embodiment of the present invention which utilizes a fired tubular reformer in combination with a mixed conducting membrane reactor.

Alternative versions of the embodiment of FIG. 4 are possible. One alternative is shown in FIG. 5 in which heat is provided to fired tubular reformer 417 by combusting fuel 501 with oxygen-depleted non-permeate 53 withdrawn from membrane reactor 43. In this alternative, compressor 409 and heat exchanger 411 of FIG. 4 are not required. All heat to heat exchangers 401, 429, and 431 is provided by flue gas 423. Stream 53 should contain enough residual oxygen to meet the requirements of fired reformer 417. Preferably, this is met by bypassing some of the oxidant around the membrane (not shown).

Figure 6:
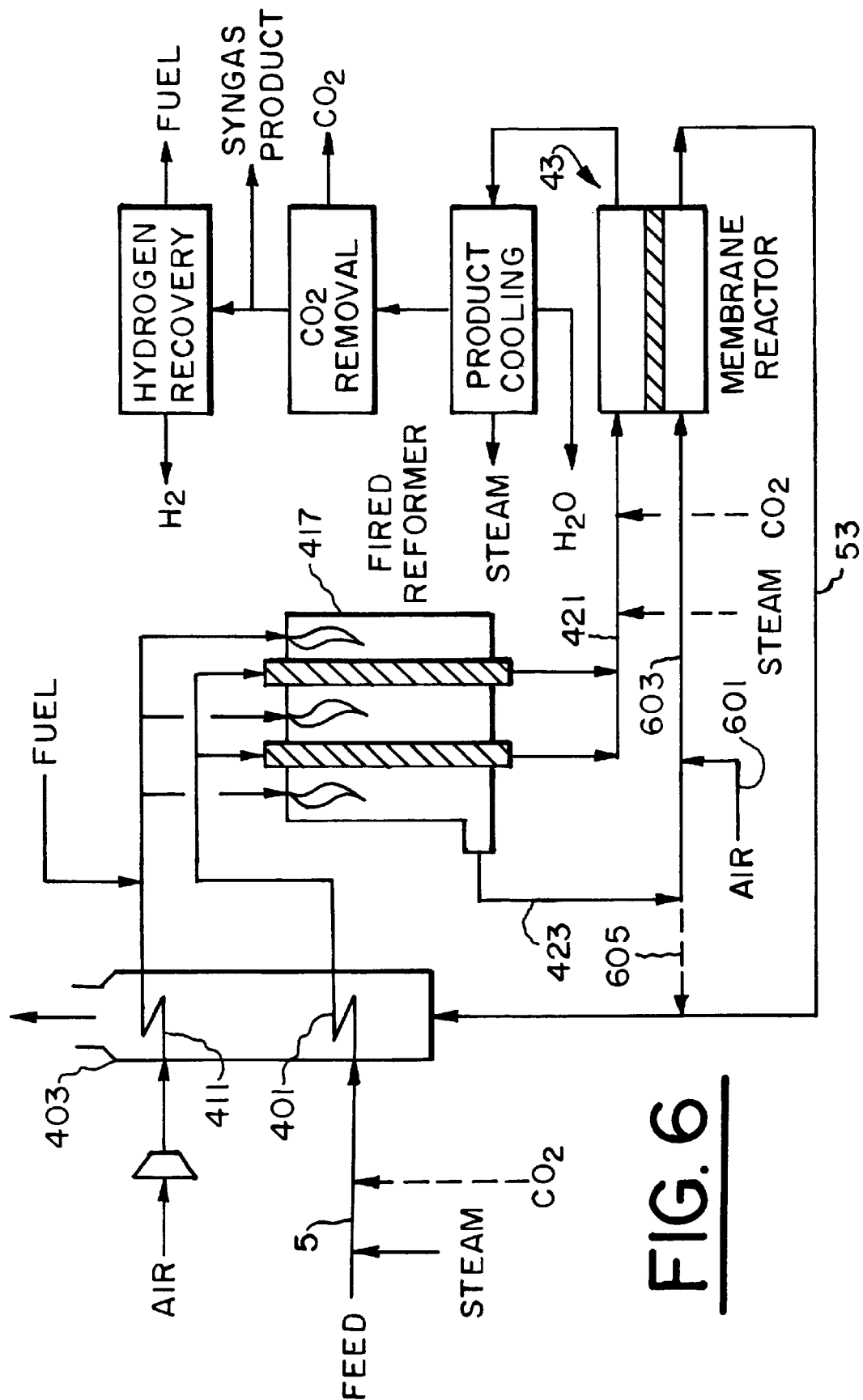
FIG. 6 is a schematic flow diagram of another alternative mode of the third embodiment of the present invention which utilizes a fired tubular reformer in combination with a mixed conducting membrane reactor.

Another alternative is shown in FIG. 6 in which flue gas 423 is withdrawn from fired tubular reformer 417, is cooled if required by the addition of cool quench air 601, and is introduced as oxygen-containing gas 603 into the oxidant side of membrane reactor 43 at the temperature earlier described. In this alternative, fired tubular reformer 417 is fired with sufficient excess air so that flue gas 423 provides the proper oxidant feed to membrane reactor 43. Depending on the flow rate of flue gas 423 and the oxidant feed requirement of membrane reactor 43, a portion 605 of flue gas 423 can bypass membrane reactor 43. In the alternative of FIG. 6 compressor 425 and heat exchangers 429 and 431 of FIG. 5 are not required. All heat for heat exchangers 401 and 411 is provided by oxygen-depleted non-permeate 53 from membrane reactor 43 and optional bypassed flue gas 605.

In an alternative to the process of FIGS. 1 through 6 described above, raw synthesis gas 51 can be quenched by direct water addition, and the resulting cooled synthesis gas introduced into one or more shift reactors to convert the carbon monoxide into additional hydrogen and carbon dioxide according to reaction (6). This shift reaction step is well-known in the art and uses iron-chromium catalyst at 650 to 850° F. (343 to 454° C.) and copper-containing catalysts at temperatures below 700° F. (371° C.). The resulting shifted gas is cooled, dewatered, and separated into a high purity hydrogen product and a purge gas containing methane and carbon dioxide. Typically, this separation is carried out by pressure swing adsorption by known methods. For hydrogen production the preferred overall steam to carbon molar ratio is 3.0 to 5.0.

Of the alternative embodiments described above, the fired tubular reformer is the most flexible in setting the inlet temperature to the membrane reactor, since fired tubular reformer outlet temperatures up to 1750° F. (954° C.) are possible. This feature is potentially very useful for mixed conducting membrane materials which may have a high activation energy and in which oxygen permeation decreases rapidly with decreasing temperature. In all the various embodiments of the present invention, the overall conversion of methane to synthesis gas is shared between the reformer (which does not require oxygen but requires steam and external heat) and the reactant side of the membrane reactor (which requires oxygen, but not heat). When the methane conversion in the reformer is increased, the methane conversion in the membrane reactor decreases, the synthesis gas product becomes richer in $H_2$, the required oxygen permeation in the membrane reactor decreases, and production of $CO_2$ decreases. Lower $CO_2$ production is generally desirable since removal is expensive. As less oxygen permeation is required, the cost of the oxidant supply to the membrane reactor decreases. However, as the methane conversion in the reformer increases, the synthesis gas product will contain an increasing amount of $H_2$. The amount of hydrogen required in this synthesis gas product will depend on the final use of the product.

The fired tubular reformer and membrane reactor steps must be operated such that the methane conversion in each step is properly balanced to meet the desired product composition. A fired tubular reformer typically is designed and operated to reach reforming equilibrium at the reactor exit temperature. As a result, the exit temperature and gas composition are coupled.

The fired tubular reformer should be operated to produce feed gas for the membrane reactor at the appropriate temperature while at the same time controlling the extent of the reforming reactions in the reformer. The fired tubular reformer can be operated to meet this requirement as follows:

1) A controlled amount of steam can be injected in the feed to the reformer (i.e. a steam to carbon molar ratio of 1.5 or less) to limit the degree of reforming; additional steam can be superheated and injected with the feed to the membrane reactor. This is applicable when the overall process steam to carbon ratio is higher than that of the fired tubular reformer.

2) Any recycled or imported carbon dioxide likewise can be heated and injected with the membrane reactor feed rather than the fired tubular reformer feed. This is favored in particular for imported carbon dioxide, since it reduces the risk of Boudouard carbon formation in the fired tubular reformer according to reaction (8) earlier presented, provided that the feed temperature to the membrane reactor is sufficiently high.

3) A portion of the mixed steam-hydrocarbon feed can bypass the fired tubular reformer entirely and be processed for heavy hydrocarbon conversion in an alternate type of reformer such as the adiabatic reformer of FIG. 1. For example, in the process of FIG. 6 a portion of steam-hydrocarbon feed mixture 5 can be processed in an adiabatic reformer (not shown) and the resulting partially reformed gas combined with fired tubular reformer product 421.

4) The catalyst tubes of the fired tubular reformer can be loaded with catalyst at the feed end and with ceramic balls at the outlet end to limit the degree of reforming while increasing the synthesis gas temperature—the radiant section of the fired reformer furnace is used in part to heat partially reformed synthesis gas. This is a novel method of operating a fired tubular reformer.

5) Commercial reformers such as those marketed by M. W. Kellogg have collection "risers" within the radiant section where the primary reformate from several tubes is further heated.

The adiabatic reformer of FIG. 1 is the simplest and cheapest reforming process to combine with a membrane reactor because it is simply a packed adiabatic reactor followed by a reheat coil. To enable use of low-alloy metallurgy in the reheat coil, and an unlined low-alloy inlet distribution system to the adiabatic reformer reactor, the reheat temperature can be limited to 1200° F. (649° C.). At this temperature, carbon formation could occur based on thermodynamics alone, but methane is a very stable molecule and requires a higher temperature to crack. The actual cracking temperature is affected by the presence of acidic refractories or nickel in the piping surfaces contacting the reactant gas.

If the membrane reactor requires higher reactant temperatures, temperatures above 1200° F. (649° C.) are possible but will require high-alloy metallurgy in the heat exchanger outlet piping and reactor inlet manifolding. Higher temperatures may be desirable to improve membrane reactor performance if the active membrane material has a high activation energy and thickness.

Maximum membrane reactor inlet temperatures can approach those furnished by a fired tubular reformer if multiple adiabatic reformers are used in series. The feed to the second reformer can be limited to 1200° F. to allow the use of favorable metallurgy in the reheat coil following the first reformer. Additional adiabatic reformers would reduce oxygen demand in the membrane reactor, but could result in an excess of hydrogen, especially if the synthesis gas is used for Fischer-Tropsch hydrocarbon synthesis. However, membrane reactor feed temperatures can be increased if necessary to enable the use of many mixed conducting membrane materials with a high degree of resistance to damage by carbon deposition. If necessary, excess hydrogen production can be minimized or eliminated by injecting a major portion of the total required steam following the reformer reactor(s). The adiabatic reformers can be operated with a steam to carbon molar ratio as low as 0.4 for natural gas feedstocks.

A summary of the differences of the reformer types described above is given in Table 1.

TABLE 1

Comparison of Reformer Types for Combination with Membrane Reactors

|  | Fired Tubular | Adiabatic | Heat Exchange |
|---|---|---|---|
| Minimum Steam to Carbon Ratio (Natural Gas Feed) | ~1.5 | 0.4 | 2.5 |
| Outlet temperature | Highest | | |
| Steam Export | Highest | Lower | Lowest |
| Thermal Efficiency | Lowest | Higher | Highest |
| Complexity | Moderate | Low | High |

TABLE 1-continued

Comparison of Reformer Types for Combination with Membrane Reactors

|  | Fired Tubular | Adiabatic | Heat Exchange |
| --- | --- | --- | --- |
| Commercial Experience | Mature | Mature | Limited |
| Operating Pressure | Lowest | High | High |

As described earlier in the review of the background art, a fired tubular reformer and an autothermal reformer can be operated in series to improve the overall efficiency of synthesis gas production. The combination of a fired tubular reformer and a mixed conducting membrane reactor of the present invention has novel features compared with the fired tubular reformer-autothermal reformer combination.

One feature is the fact that the membrane reactor produces a hot oxygen-depleted non-permeate stream not present in an autothermal reformer. As shown in the embodiments of FIGS. 4, 5, and 6, the hot non-permeate stream can be combined in several optional modes the flue gas or combustion air of the fired tubular reformer to achieve equipment consolidation and economies of scale.

Another feature of the present invention is that steam is a preferred reactant introduced into the membrane reactor with the other reactive components. This contrasts with certain of the earlier-cited background art references in which steam is considered to be a diluent in the membrane reactor feed. The present invention utilizes a selected steam to carbon ratio in the feed to first-stage steam-methane reformer as well as optionally in the partially reformed intermediate gas feed to the membrane reactor. The invention utilizes steam to moderate the exothermicity of the partial oxidation reactions, to prevent carbon formation, and to control the composition of the synthesis gas product. Temperature moderation in the feed end of the membrane reactor can be achieved by providing sufficient steam in the feed gas to ensure rapid and complete steam reforming reactions.

As the reforming and partial oxidation reactions occur through the membrane reactor, steam is beneficial in preventing carbon deposition in the catalyst by the Boudouard reaction (reaction (8) above). Steam also maintains a low concentration of unreacted methane in the synthesis gas product at the reactor exit. For example, with an overall steam to carbon molar ratio of 3.5 in the reformer/membrane reactor system, methane in the synthesis gas product can be reduced to about 0.5 vol % at 1,650° F. (899° C.). Without steam this would be achievable only at a much higher temperature. Carbon dioxide is an alternative to steam for these purposes, except for preventing Boudouard carbon formation. As explained earlier, an excess of $CO_2$ is undesirable in the synthesis gas product and excess steam is much easier to remove than excess $CO_2$.

Syngas product 67 generated by any of the process embodiments described by FIGS. 1 to 6 can be converted into liquid products such as liquid hydrocarbons or liquid oxygenated organic compounds by methods known in the art. For example, the syngas can be introduced into a Fischer-Tropsch reaction system to yield a liquid product containing hydrocarbons with greater than four carbon atoms suitable for refining into fuel products. Alternatively, the syngas can be converted in known reaction systems into liquid products such as methanol, dimethyl ether, or other oxygenated organic compounds which can be utilized as fuel, chemical intermediates, or final chemical products. Unreacted synthesis gas and/or light hydrocarbon byproducts from these reaction systems can be recycled to appropriate upstream points in the synthesis gas generation processes of FIGS. 1 to 6 to increase overall synthesis gas conversion to final products.

Syngas product 67 is introduced into a product synthesis and processing zone (not shown) which includes one or more catalytic reactors, reactor cooling systems, catalyst handling systems, reactor product cooling and separation systems, reactor feed heating systems, and optionally condensate handling and steam generation systems as required. The product synthesis and processing zone can utilize any known technology for converting syngas product 67 into a liquid product.

Conventional technology for oxygen-based synthesis gas production by partial oxidation or autothermal reforming requires an air separation unit to generate high pressure oxygen at 350 to 950 psia (24.1 to 65.5 bara) of 99.5% $O_2$. A typical power consumption for air separation using cryogenic distillation is 13 Kwh for each ton per day of capacity at 350 psia. In contrast, the power consumption in these embodiments of the present invention is estimated at 3 to 4 kwh for each ton per day of oxygen permeating in a membrane reactor. Conventional technologies (partial oxidation or autothermal reforming) generate synthesis gas at higher pressures (600 to 900 psia or 40.4 to 61.1 barg), while the synthesis gas produced by the membrane reactor of the present invention may require compression.

A conventional partial oxidation process to make synthesis gas at 900 psia (62.1 bara) to produce 2500 tons/day of methanol typically has a power requirement of about 57,000 BHP. By comparison, a membrane reactor system is estimated to produce the same synthesis gas product with an overall power consumption of about 26,000 BHP for the system of FIG. 1 and 24,000 BHP for the system of FIG. 2. These power figures include synthesis gas product compression.

Such power and energy savings can be achieved with the present invention by a careful selection of preferred (but not required) operating conditions including: (1) providing air feed to the membrane reactor at near-ambient pressure; (2) providing reactant gas to the membrane reactor at an elevated pressure preferably above 200 psig (13.8 barg); (3) recovering greater than 90% of the oxygen by permeation across the membrane in the membrane reactor; and (4) using partial reforming with heat integration wherein the hot membrane reactor permeate and non-permeate gas heats the air and reactant gas streams. If the mixed conducting membrane in the membrane reactor must withstand a positive trans-membrane pressure differential from the reactant side to the oxidant side, this can be accomplished for example by using the asymmetric membrane structure known in the art as disclosed in U.S. Pat. Nos. 5,599,383 and 5,681,373 cited earlier.

Prior art mixed conducting membrane reactors utilize low, near-ambient gas pressures on both sides of the membrane, which would require product compression for most practical synthesis gas applications. In the example described above for a 2500 ton per day methanol plant, such a prior art membrane reactor could require more power than the conventional partial oxidation process discussed above.

EXAMPLE 1

The process of FIG. 1 for producing synthesis gas from natural gas is illustrated by a heat and material balance in the following example. The synthesis gas product 67 has a molar hydrogen/CO ratio of 2.15 and is suitable for further compression and use in the Fischer-Tropsch process for hydrocarbon synthesis. Natural gas at about 350 psia is mixed with recycled hydrogen from hydrogen recovery system 71 to yield 3 mole % hydrogen in the feed mixture. This feed is preheated against membrane reactor non-permeate in heat exchange zone 8 to about 700° F., hydrogenated, and desulfurized to remove olefins and sulfur compounds as earlier described to provide reactant feed gas 1. Reactant feed gas 1 is mixed with steam 3 to give a steam/carbon molar ratio of 1.6, preheated in heat exchanger 7 to 1022° F., and fed to adiabatic reformer reactor 13. Carbon conversion in the reactor is 7% and all hydrocarbons heavier than methane are converted to methane, hydrogen, and carbon oxides. The temperature decreases to 885° F. across adiabatic reformer reactor 13 due to the net endothermic reactions occurring therein. Partially reformed synthesis gas 17 is mixed with carbon dioxide 19 which is recycled as part of carbon dioxide 65, the gas is further heated cocurrently in heat exchanger 23 to 1200° F., and the heated gas is introduced into reactant side 47 of membrane reactor 43.

Air 27 is compressed in blower 29 to 24.7 psia and the resulting compressed air 31 passes directly to burner 39 for combustion with fuel gas 37 (heat exchanger 33 is not used). The resulting heated air at 1200° F. flows into oxidant side 45 of membrane reactor 43. About 240 million Btu/hr of fuel is required and a portion of this is provided by fuel 75 which is the reject gas from hydrogen recovery system 71. The oxygen content of heated air 41 is 16 mole % and the oxygen content of non-permeate 53 is less than 2 mole %. Non-permeate 53 at 1742° F. flows to heat exchange zone 8, cools by supplying heat to heat exchangers 7 and 23, and is further cooled to preheat the natural gas feed (not shown). The resulting cooled gas is discharged to the atmosphere as flue gas 10.

Raw synthesis gas product 51 is withdrawn from membrane reactor 43 at 1742° F. and is processed as earlier described in product cooling zone 55 to yield cooled and dewatered synthesis gas 61. A small portion (about 2% of the flow) of cooled and dewatered synthesis gas 61 is taken directly to hydrogen recovery system 71 and separated to provide hydrogen 73 for the pretreatment of feed 1 as earlier described. 77% of the remaining cooled and dewatered synthesis gas 61 is processed in carbon dioxide removal system 63 to recover the amount of carbon dioxide 65 needed for recycle as carbon dioxide 19 to obtain the desired molar hydrogen/CO ratio of 2.15 in the final synthesis gas product. The rest (23%) of the remaining cooled and dewatered synthesis gas 61 bypasses carbon dioxide removal system 63 and is blended back to yield the final synthesis gas product 67 which contains 4 mole % carbon dioxide and 0.5 mole % methane.

A summary of the stream properties of Example 1 is given in Table 2.

TABLE 2

Process Stream Information (Example 1)

| Steam No. (FIG. 1) Stream Description | 1 Feed | 3 Process Steam | 11 Reformer Inlet | 17 Reformer Outlet | 25 Membrane Reactor Inlet | 51 Membrane Reactor Outlet | 61 Raw Syngas | 67 Syngas Product | 19 $CO_2$ Recycle | 37 Burner Fuel Import | 27 Oxidant Feed | 53 Reactor Oxidant Outlet |
|---|---|---|---|---|---|---|---|---|---|---|---|---|
| T, ° F. | 700 | 700 | 1022 | 885 | 1200 | 1742 | 100 | 100 | | 100 | 100 | 1,742 |
| P, psia | 350 | 400 | | 300 | | 265 | | 225 | 2325 | | 14.7 | |
| Total Flow, (lb moles/hr) | 6,981 | 11,265 | 18,247 | 19,222 | 21,940 | 34,837 | 23,003 | 19,825 | 2,718 | 559 | 28,397 | 24,807 |
| Component Flow (lb moles/hr) | | | | | | | | | | | | |
| Nitrogen | 21 | | 21 | 21 | 21 | 21 | 21 | 21 | | 1.7 | 22,178 | 22,180 |
| Oxygen | | | | | | | | | | | 5,963 | 496 |
| Argon | | | | | | | | | | | 256 | 256 |
| Hydrogen | 209 | | 209 | 1796 | 1796 | 13,091 | 13,089 | 12,827 | | | | |
| Carbon monoxide | | | | 15 | 15 | 6,085 | 6,084 | 5,963 | | | | |
| Carbon dioxide | 59 | | 59 | 531 | 3,249 | 3,628 | 3,610 | 819 | 2,718 | 4.9 | | 639 |
| Water | | 11,265 | 11,265 | 10,306 | 10,306 | 11,908 | 95 | 95 | | | | 1,237 |
| Methane | 6,456 | | 6,456 | 6,553 | 6,553 | 105 | 105 | 103 | | 533.0 | | |
| Ethane | 171 | | 171 | (1) | (1) | | 105 | 103 | | 14.1 | | |
| Propane | 37 | | 37 | | | | | | | 3.1 | | |
| Butane | 15 | | 15 | | | | | | | 1.2 | | |
| Pentane | 5 | | 5 | | | | | | | 0.5 | | |
| $C_{6+}$ | 7 | | 7 | | | | | | | 0.7 | | |

(1) Concentration <100 ppm

EXAMPLE 2

Process heat and material balance calculations were carried out to compare the performance of a mixed conducting membrane reactor system with and without a first stage reformer preceding the membrane reactor. The comparison was based on synthesis gas required for the production of 2,500 tons/day of methanol.

The synthesis gas is provided at a pressure of 210 psig and has a stoichiometric number of 2.0 (defined as the molar ratio $[H_2-CO_2]/[CO+CO_2]$) which is required for methanol production. The stoichiometric number is controlled by the amount of carbon dioxide removed from the raw synthesis gas product. The mixed conducting membrane reactor system operates at a synthesis gas outlet temperature of 1650° F. (900° C.) and outlet pressure of 250 psig (17.2 barg). The oxygen concentration in the non-permeate stream from the membrane reactor is 2.0 mole % in all cases. The steam-to-carbon ratio of the reactant feed is adjusted in each case such that the residual methane in the final synthesis gas product is about 0.5 mole % (dry basis). The membrane reactor inlet temperature on both the oxidant (air) side and the reactant side are fixed at 1022° F. (550° C.) for the membrane reactor alone without a first stage reformer, 1200° F. for the adiabatic reformer-membrane reactor system, and 1150° F. for the heat transfer reformer-membrane reactor case. 1150° F. is the maximum preheat possible to preserve a 104° F. temperature approach at inlet end of the heat transfer reformer, since the feed was not subsequently reheated.

A comparison of operating parameters is given in Table 3 for a membrane reactor system without a first stage reformer, a combined adiabatic reformer/membrane reactor system (FIG. 1), and a combined heat transfer reformer/membrane reactor system (FIG. 2). It is seen that a reforming step prior to the membrane reactor reduces the amount of oxygen required in the reactor, since a substantial portion of the synthesis gas production is shifted out of the membrane reactor into the reformer, the heat duty for which is supplied externally.

TABLE 3

Process Parameters (Example 2)

|  | No Reformer | Adiabatic Reformer (FIG. 1) | Heat Transfer Reformer (FIG. 2) |
|---|---|---|---|
| Synthesis Gas Product, lb moles/hr | 23,858 | 24,177 | 24,327 |
| Synthesis Gas Composition, Mole % (Dry) |  |  |  |
| Methane | 0.5 | 0.5 | 0.5 |
| Carbon Monoxide | 16.5 | 15.3 | 14.7 |
| Carbon Dioxide | 12.4 | 13.3 | 13.7 |
| Hydrogen | 70.1 | 70.4 | 70.6 |
| Carbon Dioxide Removed, lb moles/hr | 855 | 351 | None |
| Oxygen Permeated, short tons/day | 1,865 | 1,489 | 1,225 |
| Natural Gas Reactant, million BTU/hr HHV | 2,959 | 2,777 | 2,649 |
| Natural Gas Fuel, million BTU/hr HHV | 273 | 421 | 182 |
| Steam Export, Klb/hr (350 psig, 436° F., Sat.) | 140 | 109 | −227 |
| Power Consumption, BHP | 10,050 | 7,910 | 6,100 |

A reduced oxygen requirement translates into reduced air handling equipment (compression and heat exchange), air compression power, and possibly membrane area. Since less oxygen is consumed in the reactions occurring in the membrane reactor, which operates under conditions of nearly complete hydrocarbon conversion, less carbon monoxide is consumed to make carbon dioxide, and therefore the size of the expensive carbon dioxide removal system decreases significantly. In the combined heat transfer reformer/membrane reactor system (FIG. 2), no carbon dioxide removal is needed.

Thus the process of the present invention allows the generation of synthesis gas from a wide selection of hydrocarbon feedstocks with significant potential for power reduction compared with prior art processes. The operation of a steam reforming step in series with a mixed conducting membrane reactor is a unique combination which allows the strategic use of steam as a reactant in both the steam reforming reactor and the membrane reactor. The use of steam has a number of benefits including moderation of the exothermicity of the partial oxidation reactions, prevention of carbon formation, and control of the composition of the synthesis gas product.

Several types of steam reforming reactors can be integrated with the membrane reactor of the present invention, and various alternative modes of integration are possible between the steam reforming and membrane reactors. Heat integration of the steam reforming and membrane reactors contributes to the overall efficiency of the process.

The essential characteristics of the present invention are described completely in the foregoing disclosure. One skilled in the art can understand the invention and make various modifications without departing from the basic spirit of the invention, and without deviating from the scope and equivalents of the claims which follow.

What is claimed is:

1. A method for the production and utilization of synthesis gas containing hydrogen and carbon monoxide which comprises:

(a) providing a catalytic reforming reaction zone comprising at least one catalyst which promotes the steam reforming of hydrocarbons;

(b) heating a reactant gas feed comprising steam and one or more hydrocarbon compounds having two or more carbon atoms, introducing the resulting heated reactant gas feed into the catalytic reforming reaction zone, and withdrawing therefrom a partially reformed intermediate gas comprising at least methane, hydrogen, and carbon oxides;

(c) providing a mixed conducting membrane reaction zone having an oxidant side and a reactant side which are separated by a solid mixed conducting membrane;

(d) heating an oxygen-containing oxidant gas feed and introducing the resulting heated oxidant gas feed into the oxidant side of the mixed conducting membrane reactor;

(e) introducing the partially reformed intermediate gas into the reactant side of the mixed conducting membrane reactor;

(f) permeating oxygen from the oxidant side of the mixed conducting membrane reactor through the mixed conducting membrane to the reactant side of the mixed conducting membrane reactor and reacting the oxygen with the partially reformed intermediate gas to form additional hydrogen and carbon monoxide;

(g) withdrawing a raw synthesis gas product comprising hydrogen, carbon monoxide, carbon dioxide, and water from the reactant side of the mixed conducting membrane reactor;

(h) withdrawing an oxygen-depleted nonpermeate gas from the oxidant side of the mixed conducting membrane reactor;

(i) treating the raw synthesis gas to remove at least a portion of a component other than hydrogen and carbon monoxide to yield a final synthesis gas product, and (j) providing a product synthesis and processing zone and converting at least a portion of the final synthesis gas product therein to yield a liquid product.

2. The method of claim 1 which further comprises the step of heating the partially reformed intermediate gas.

3. The method of claim 1 wherein the reactant gas feed comprises methane.

4. The method of claim 1 wherein at least a portion of the heat for heating the oxygen-containing oxidant gas feed is provided by indirect heat exchange with at least a portion of the oxygen-depleted nonpermeate gas from the oxidant side of the mixed conducting membrane reactor.

5. The method of claim 1 wherein at least a portion of the heat for heating the reactant gas feed is provided by indirect heat exchange with at least a portion of the oxygen-depleted nonpermeate gas from the oxidant side of the mixed conducting membrane reactor.

6. The method of claim 1 wherein at least a portion of the heat for heating the oxygen-containing oxidant gas feed is provided by direct combustion of a portion of the oxidant gas feed with a fuel gas.

7. The method of claim 1 wherein at least a portion of the oxygen-depleted nonpermeate gas is cooled by indirect heat transfer with one or more gas streams selected from the group consisting of the oxygen-containing oxidant gas feed, the reactant gas feed, and the partially reformed intermediate gas.

8. The method of claim 1 wherein at least a portion of the carbon monoxide in the raw synthesis gas product is converted to hydrogen and carbon dioxide by contacting the raw synthesis gas with a shift catalyst.

9. The method of claim 1 wherein the catalytic reforming reaction zone comprises at least one catalytic reforming reactor which is operated adiabatically.

10. The method of claim 9 wherein the oxygen-containing oxidant gas feed comprises a gas selected from the group consisting of air and a flue gas produced by combusting a fuel in excess air.

11. The method of claim 9 wherein at least a portion of the heat for heating the oxygen-containing oxidant gas feed is provided by direct combustion of a portion of the oxidant gas feed with a fuel gas.

12. The method of claim 9 wherein one or more additional reactants selected from the group consisting of steam and carbon dioxide are added to the partially reformed intermediate gas.

13. The method of claim 1 wherein the catalytic reforming reaction zone comprises a heat exchanged catalytic reforming reactor wherein heat is provided within the reactor by indirect heat exchange with at least a portion of the raw synthesis gas product.

14. The method of claim 13 wherein at least a portion of the oxygen-depleted nonpermeate gas is cooled by indirect heat transfer with one or more gas streams selected from the group consisting of the oxygen-containing oxidant gas feed and the reactant gas feed.

15. The method of claim 13 wherein the oxygen-containing oxidant gas feed comprises a gas selected from the group consisting of air and a flue gas produced by combusting a fuel in excess air.

16. The method of claim 13 wherein at least a portion of the heat for heating the oxygen-containing oxidant gas feed is provided by direct combustion of a portion of the oxidant gas feed with a fuel gas.

17. The method of claim 13 wherein one or more additional reactants selected from the group consisting of steam and carbon dioxide are added to the partially reformed intermediate gas.

18. The method of claim 1 wherein the catalytic reforming reaction zone comprises a fuel-fired catalytic reforming reactor wherein heat is provided within the reactor by indirect heat exchange with combustion products formed by the combustion of a fuel and an oxygen-containing reformer combustion gas, and wherein a reforming reactor flue gas is withdrawn therefrom.

19. The method of claim 18 wherein at least a portion of the oxygen-depleted nonpermeate gas is cooled by indirect heat transfer with one or more gas streams selected from the group consisting of the oxygen-containing oxidant gas feed, the oxygen-containing reformer combustion gas, and the reactant gas feed.

20. The method of claim 18 wherein at least a portion of the reforming reactor flue gas is cooled by indirect heat transfer with one or more gas streams selected from the group consisting of the oxygen-containing oxidant gas feed, the oxygen-containing reformer combustion gas, and the reactant gas feed.

21. The method of claim 18 wherein at least a portion of the heat for heating the oxygen-containing oxidant gas feed is provided by direct combustion of a portion of the oxidant gas feed with a fuel gas.

22. The method of claim 18 wherein carbon dioxide is added to the reactant gas feed.

23. The method of claim 18 wherein one or more additional reactants selected from the group consisting of steam and carbon dioxide are added to the partially reformed intermediate gas.

24. The method of claim 18 wherein at least a portion of the oxygen-containing reformer oxidant gas is provided by at least a portion of the oxygen-depleted nonpermeate gas.

25. The method of claim 18 wherein the oxygen-containing oxidant gas feed comprises a gas selected from the group consisting of air and a flue gas produced by combusting a fuel in excess air.

26. The method of claim 18 wherein at least a portion of the heated oxidant gas feed into the oxidant side of the mixed conducting membrane reactor is provided by at least a portion of the reforming reactor flue gas.

27. The method of claim 26 wherein a stream of air is introduced into the heated oxidant gas feed prior to the oxidant side of the mixed conducting membrane reactor, wherein the stream of air is at a temperature below the temperature of the heated oxidant gas feed.

28. The method of claim 1 wherein reactant side of the mixed conducting membrane reactor contains a reforming catalyst.

29. The method of claim 1 wherein the liquid product contains one or more components selected from the group consisting of hydrocarbons containing greater than four carbon atoms, methanol, and dimethyl ether.

* * * * *